United States Patent
Mann et al.

(10) Patent No.: US 9,290,463 B2
(45) Date of Patent: Mar. 22, 2016

(54) RADIOLABELED COMPOUNDS AND USES THEREOF

(71) Applicant: THE TRUSTEES OF COLUMBIA UNIVERSITY IN THE CITY OF NEW YORK, New York, NY (US)

(72) Inventors: Joseph John Mann, Riverdale, NY (US); J. S. Dileep Kumar, Fort Lee, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 60 days.

(21) Appl. No.: 13/668,975

(22) Filed: Nov. 5, 2012

(65) Prior Publication Data

US 2013/0156699 A1   Jun. 20, 2013

Related U.S. Application Data

(63) Continuation-in-part of application No. PCT/US2011/035385, filed on May 5, 2011.

(60) Provisional application No. 61/331,670, filed on May 5, 2010.

(51) Int. Cl.
| | |
|---|---|
| *A61K 51/04* | (2006.01) |
| *C07D 253/075* | (2006.01) |
| *C07B 59/00* | (2006.01) |
| *C07D 401/14* | (2006.01) |
| *C07D 403/06* | (2006.01) |

(52) U.S. Cl.
CPC ........ *C07D 253/075* (2013.01); *A61K 51/0461* (2013.01); *C07B 59/002* (2013.01); *C07D 401/14* (2013.01); *C07D 403/06* (2013.01)

(58) Field of Classification Search
CPC .... A61K 51/00; C07D 401/14; C07D 403/06; A61P 25/00
USPC .................. 424/1.89, 1.85, 1.81; 514/242
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,431,922 A | 7/1995 | Nicklasson | |
| 5,591,767 A | 1/1997 | Mohr et al. | |
| 5,609,849 A * | 3/1997 | Kung ................... | 424/1.85 |
| 5,633,009 A | 5/1997 | Kenealy et al. | |
| 5,639,476 A | 6/1997 | Oshlack et al. | |
| 5,674,533 A | 10/1997 | Santus et al. | |
| 5,698,155 A | 12/1997 | Grosswald et al. | |
| 5,733,556 A | 3/1998 | Schrier et al. | |
| 5,859,014 A | 1/1999 | Bantle et al. | |
| 5,977,106 A | 11/1999 | Patoiseau et al. | |
| 6,008,222 A | 12/1999 | Salazar | |
| 8,168,786 B2 | 5/2012 | Mann et al. | |
| 2005/0187226 A1 | 8/2005 | Wilson et al. | |
| 2008/0138283 A1 | 6/2008 | Mann et al. | |

FOREIGN PATENT DOCUMENTS

| | | | |
|---|---|---|---|
| WO | WO-2006/083424 | | 8/2006 |
| WO | WO-2006083424 | * | 8/2006 |
| WO | WO-2009/006227 | | 1/2009 |
| WO | WO-2011/140360 | | 11/2011 |

OTHER PUBLICATIONS

Eleanor S. Prochaska et al. Matrix Reactions of Fluorine with Chlorine, Bromine, Iodine. Infrared Detection of the XF2, X2F2, and X2F species, Inorganic Chemistry, vol. 17(4), 970-977, 1978.*

Suzuki, Akira, "Synthetic studies via the cross-coupling reaction of organoboron derivatives with organic hallides", *Pure Appl. Chem.* 1991, vol. 63, No. 3, pp. 419-422.

Buchwald, Henry, et al., "Long-term, continuous intravenous heparin administration by an implantable infusion pump in ambulatory patients with recurrent venous thrombosis", Surgery, vol. 88, pp. 507-516 (Oct. 1980).

Smolen, Victor F., et al., "Controlled Drug Bioavailability, Drug Product Design and Performance", John Wiley & Sons, 1984, Table of Contents, 3 pages.

During, Matthew J., et al., "Controlled Release of Dopamine from a Polymeric Brain Implant: In Vivo Characterization", Ann. Neural., Apr. 1989, vol. 25, No. 4, pp. 351-356.

Molander, Gary A., "Potassium trifluoroborate salts as convenient, stable reagents for difficult alkyl transfers", Curr. Opin. Drug Discov. Devel. 2009, vol. 12, No. 6, pp. 811-823.

Howard, Matthew A., et al., "Intracerebral drug delivery in rats with lesion-induced memory deficits", J. Neurosurg., Jul. 1989, vol. 71, pp. 105-112.

Stille, John K., "The Palladium-Catalyzed Cross-Coupling Reactions of Organotin Reagents with Organic Electrophiles", *Angew. Chem. Int. Ed.*, 1986, vol. 25, pp. 508-524.

Kumar, J. S. Dileep, et al., "Synthesis and in vivo validation of [O-Methyl-$^{11}$C]2-{4-[4-(7-methoxynaphthalen-1-yl)piperazin-1-yl]butyl}-4-methyl-2H-[1,2,3]traizine-3,5-dione: A novel 5-HT$_{1A}$ Receptor agonist positron emission tomography ligand," J. Med Chem., vol. 49, pp. 125-134 (2006).

(Continued)

*Primary Examiner* — Michael G Hartley
*Assistant Examiner* — Jagadishwar Samala
(74) *Attorney, Agent, or Firm* — Wilmer Cutler Pickering Hale and Dorr LLP

(57) ABSTRACT

The present invention relates to Radiolabeled Compounds labeled with fluorine, bromine, iodine, carbon, or tritium isotopes and methods of use thereof for treating or preventing a psychiatric disorder in a subject, for stabilizing the mood of a subject having a mood disorder, or as imaging agents for a serotonin receptor. Compositions comprising an imaging-effective amount of a Radiolabeled Compound are also disclosed.

13 Claims, 3 Drawing Sheets
(3 of 3 Drawing Sheet(s) Filed in Color)

(56) References Cited

OTHER PUBLICATIONS

Kumar, J. S. Dileep, et al., "Synthesis and in vivo evauaItion of a novel 5-HT$_{1A}$ receptor agonist radioligand [O-methyl-$^{11}$C]2-(4-(4-(2-methoxyphenyl) piperazin-1-yl)butyl)-4-methyl-1,2,4-triazine-3,5(2H,4H)dione in nonhuman primates," Eur. J. Nucl. med. Mol. Imaging, vol. 34, pp. 1050-1060 (2007).

Langer, Robert, "New Methods of Drug Delivery", Science, vol. 249, pp. 1527-1533 (Sep. 28, 1990).

Levy, Robert, et al., "Inhibition of Calcification of Bioprosthetic Heart Valves by Local Controlled-Release Diphosphonate", Science, vol. 228, pp. 190-192 (Apr. 12, 1985).

Treat, Joseph, et al., "Liposome Encapsulated Doxorubicin Preliminary Results of Phase I and Phase II Trials", Liposomes in the Therapy of Infectious Disease and Cancer, pp. 353-365 (1989).

Kumada, Makoto, "Nickel and Palladium Complex Catalyzed Cross-Coupling Reactions of Organometallic Reagents with Organic Halides", *Pure Appl. Chem.* 1980, vol. 52, pp. 669-679.

Majo, Vattoly J., et al., "Synthesis and evaluation of [O-methyl-$^{11}$C]4-[3-[4-(2-methoxyphenyl)-piperazin-1-yl]propoxy]-4-azatricyclo[5.2.1.02,6]dec-8-ene-3,5-dione as a 5-HT$_{1A}$ receptor agonist PET ligand," Journal of Labelled Compounds and Radiopharmaceuticals, vol. 51, pp. 132-136 (2008).

Langer, Robert S., et al., "Medical Applications of Controlled Release, vol. I Classes of Systems", CRC Press, Inc., Boca Raton, Florida, 1984, Table of Contents, 4 pages.

Milak, Miatthew S., et al., "In vivo Quantification of Human Serotonin 1A Receptor Using $^{11}$C-CUMI-101, an Agonist PET Radiotracer," The Journal of Nuclear medicine, vol. 51, pp. 1892-1900 (2010).

Milak, Matthew S., et al., "In vivo serotonin-sensitive binding of [$^{11}$C]CUMI-101: a seotonin 1A receptor agonist positron emission tomography radiotracer," J. of Cerebral Blood Flow & metabolism, vol. 31, pp. 243-249 (2001).

Milak, Matthew S., et al., "Modeling considerations for $^{11}$C-CUMI-101, an agonist radiotracer for imaging serotonin 1A Receptor in vivo with PET," J. Nucl. Med, vol. 49, pp. 587-596 (2008).

Prabhakaran, Jaya, et al., "Synthesis, in vitro and in vivo evolution of [O-methyl-$^{11}$C]2-{4-[4-(3-methoxyphenyl)piperazin-1*-yl]-butyl-4-methyl-2H-[1,2,4]-triazine-3,5-diones: A novel agonist 5-HT$_{1A}$ receptor PET ligand," Bioorg. Med. Chem. Lett., vol. 16, pp. 2101-2104 (2006).

Langer, Robert et al., "Chemical and Physical Structure of Polymers as Carriers for Controlled Release as Carriers for Controlled Release of Bioactive Agents: A Review", JMS-Rev. Macromol. Chem. Phys., 1983, vol. C23, No. 1, pp. 61-126.

Saudek, Christopher D. et al., "A Preliminary Trial of the Programmable Implantable Medication System for Insulin Delivery", N. Engl. J Med. 321, pp. 574-579 (Aug. 31, 1989).

Sefton, CRC Critical Reviews in Biomedical Engineering, vol. 14, Issue 3, pp. 201-240 (1987).

De Vries, erik F. J., et al., "Synthesis and In Vivo Evaluation of $^{18}$F-Desbromo-DuP-697 as a PET Tracer for Cyclooxygenase-2 Expression", Journal of Nuclear Medicine,vol. 44, No. 10, pp. 1700-1706 (Oct. 2003).

Aouizerate et al., "Updated overview of the putative role of the serotoninergic system in obsessive-compulsive disorder," Neuropsychiatric Disease and Treatment, vol. 1(3); pp. 231-243 (2005).

Aznavour et al., "A comparison of in vivo and in vitro neuroimaging of 5-HT1A receptor binding sites in the cat brain," Journal of Chemical Neuroamatony, vol. 31, pp. 226-232 (2006).

Bailer et al., "Altered Brain Serotonin 5-HT1A receptor binding after recovery from anorexia nervosa measured by positron emission tomography and [Carbonyl11C]WAY-100635," Arch Gen Psychiatry, vol. 62, pp. 1032-1041 (2005).

Blier et al., "The importance of serotonin and noradrenaline in anxiety," International Journal of Psychiatry in Clinical Practice, vol. 11, pp. 16-23 (2007).

Bonne et al., "No change in Serotonin type 1A receptor binding in Patients with posttraumatic stress disorder," Am J. Psychiatry, vol. 162, pp. 383-385 (2005).

Brett et al., "Exclusion of the 5-HT1A Serotonin Neuroreceptor and tryptophan Oxygenase Genes in a large British kindred multiply affected with tourette's Syndrome, Chronic motor tics, and obsessive-compulsive behavior," Am. J. Psychiatry, vol. 152; pp. 437-440 (Mar. 1995).

Cleare et al., "Brain 5-HT1A Receptor binding in chronic fatigue syndrome measured using positron emission tomography and [11C]Way-100635," Biol psychiatry, vol. 57, pp. 239-246 (2005).

Colpaert et al., "5-HT1A receptor in chronic pain processing and control," Proceedings of the World Congress on Pain, 11th, Sydney, Australia, Aug. 21-26, 2005 (2006), Meeting Date, pp. 147-154.

International Search Report and Written Opinion for International Patent Application No. PCT/US2008/068408, 7 pages.

International Search Report for International Application No. PCT/US2005/046565, 2 pages, Aug. 10, 2006.

Crocq et al., "Clinical potentialities and perspectives for the use of aripiprazole in other disorders than its classical indications. A critical analysis of the recent literature," L'Encephale, vol. 34, pp. 187-193 (2008).

Dannon et al., "Pindolol augmentation in treatment-resistant obsessive compulsive disorder: a double-blind placebo controlled trial," European Neuropsychopharmacology, vol. 10, pp. 165-169 (2000).

Derry et al., "Increased serotonin receptor availability in human sleep: Evidence from an [18F]MPPF study in narcolepsy," NeuroImage, vol. 30, pp. 341-348 (2006).

Doder et al., "Tremor in Parkinson's disease and serotonergic dysfunction: An 11C-WAY 100635 PET study," Neurology, vol. 60, pp. 601-605 (2003).

Drevets et al., "PET imaging of Serotonin 1A Receptor binding in Depression," Biol Psychiatry, vol. 46, pp. 1375-1387 (1999).

El Mansari et al., "Responsiveness of 5-HT1A and 5-HT2 receptors in the rat orbitofrontal cortex after long-term serotonin reuptake inhibition," Rev. Psychiatr. Neurosci, vol. 30, pp. 268-274 (2005).

Giovacchini et al., "5-HT1A Receptor are reduced in temporal lobe epilepsy after partial-Volume correction," The journal of Nuclear Medicine, vol. 46, pp. 1128-1135 (Jul. 2005).

International Search Report and Written Opinion mailed on Jul. 27, 2011 for International Application No. PCT/US11/35385 filed May 5, 2011, 10 pages.

Ito et al., Changes in central 5-HT1A receptor binding in mesial temporal epilepsy measured by positron emission tomography with [11C]WAY100635, Epilepsy Res. vol. 73, pp. 111-118 (2007).

Kepe et al., "Serotonin 1A receptors in the living brain of Alzheimer's disease patients," PNAS, vol. 103, pp. 702-707 (Jan. 2006).

Kumar et al., "PET tracers for 5-HT1a receptors and uses thereof," Drug Discovery today, vol. 12, pp. 748-756 (2007).

Lanzenberger et al., "Reduced Serotonin-1A Receptor Binding in Social Anxiety Disorder," Biol Psychiatry, vol. 61, pp. 1081-1089 (2007).

Lesch et al., "Long-Term fluoxetine treatment decreases 5-HT1A receptor responsivity in obsessive-compulsive disorder," Psychopharmacology vol. 105; pp. 415-420 (1991).

Lesch et al.,"5-Hydroxytryptamine1A Receptor responsivity in obsessive-compulsive disorder. Comparison of Patients and Controls," Arch Gen Psychiatry, vol. 48; pp. 540-547 (1991).

Matsushita et al., "Perospirone, a novel antipsychotic drug, inhibits marble-burying behavior via 5-HT1A Receptor in mice: implication for obsessive-compulsive disorder," J. Pharmacol Sci, vol. 99, pp. 154-159 (2005).

Meltzer et al., "Serotonin IA Receptor binding and treatment response in late-life depression," Neuropsychopharmacology, vol. 29, pp. 2258-2265 (2004).

Merlet et al., "5-HT1A receptor binding and intracerebral activity in temporal lobe epilepsy: an [18F]MPPF-PET study," Brain, vol. 127, pp. 900-913 (2004).

Meschaks et al., "Regional Reductions in Serotonin 1A Receptor binding in Juvenile Myoclonic Epilepsy," Arch. Neurol. vol. 62, pp. 946-950 (2005).

(56) References Cited

OTHER PUBLICATIONS

Muller et al., "Serotonin and psychostimulant addiction: Focus on 5-HT1A-receptors," Progress in Neurobiology, vol. 81, pp. 133-178 (2007).

Neumeister et al., "Reduced serotonin type 1A Receptor binding in panic disorder," The Journal of Neuroscience, vol. 24(3); pp. 589-591 (2004).

Parsey et al., "Altered Serotonin 1A Binding in major Depression: A [carbonyl-C-11]WAY100635 positron emission tomography study," Biol Psychiatry, vol. 59, pp. 106-113 (2006).

Parsey et al., "Higher 5-HT1A Receptor binding potential during a major depressive episode predicts poor treatment response: Preliminary data from a Naturalistic study," Neuropsychopharmacology, vol. 31, pp. 1745-1749 (2006).

Pimlott SL., Radiotracer Development in Psychiatry, Nucl. Med. Commun. 26(3): 183-188, 2005, 2 pgs.

Price et al., "Evidence of increased serotonin-!A receptor binding in type 2 diabetes: a positron emission tomography study," Brain Research, vol. 927, pp. 97-103 (2002).

Savic et al., "Limbic reductions of 5-HT1A receptor binding in human temporal lobe epilepsy," Neurology, vol. 62, pp. 1343-1351 (2004).

Sullivan et al., "Brain Serotonin 1A Receptor binding in major depression is related to Psychic and somatic anxiety," Biol Psychiatry, vol. 58, pp. 947-954 (2005).

Tauscher et al., "Brain Serotonin 5-HT1A receptor binding in schizophrenia measured by positron emission tomography and [11C]WAY-100635," Arch Gen Psychiatry, vol. 59, pp. 514-520 (2002).

Theodore et al., "The Effect of Antiepileptic drugs on 5-HT1A-Receptor binding measured by positron emission tomography," Epilepsia, vol. 47(3), pp. 499-503 (2006).

Tiihonen et al., "Brain Serotonin 1A Receptor binding in Bulimia nervosa," Biol Psychiatry, vol. 55, pp. 871-873 (2004).

Turner et al., "[11C]-way 100635 PET demonstrates marked 5-HT1A receptor changes in sporadic ALS," Brain, vol. 128, pp. 896-905 (2005).

Udo de Haes et al., "Effect of Fenfluramine-Induced Increases in Serotonin Release on [18F]MPPF Binding: A Continuous Infusion PET Study in Conscious Monkeys," Synapse, vol. 59, pp. 18-26 (2006).

Weiss et al., "Language lateralization in unmedicated patients during an acute episode of schizophrenia: A Functional MRI Study," Psychiatry Research: Neuroimaging, vol. 146, pp. 185-190 (2006).

Woods et al., "Selective Serotonin re-uptake inhibitors decrease schedule-induced poly-dipsia in rats: a potential model for obsessive compulsive disorder," Psychopharmacology, vol. 112, pp. 195-198 (1993).

Yasuno et al., Decreased 5-HT1A Receptor Binding in Amygdala of Schizophrenia, Biol Psychiatry, vol. 55, pp. 439-444 (2004).

* cited by examiner

RADIOLABELED COMPOUNDS AND USES THEREOF

This application is a continuation-in-part of International Application Number PCT/US2011/035385, filed on May 5, 2011, which claims priority to U.S. Provisional Patent Application No. 61/331,670, filed on May 5, 2010, the contents of which are hereby incorporated by reference herein in their entireties.

This application is related to U.S. patent application Ser. No. 11/823,641, filed Jun. 28, 2007, which claims the benefit of the earlier filing date of U.S. Patent Application No. 60/639,457, filed on Dec. 28, 2004, the contents of which are hereby incorporated by reference herein in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

The present invention relates to Radiolabeled Compounds and methods of use thereof for treating or preventing a psychiatric disorder in a subject, for stabilizing the mood of a subject having a mood disorder, or as imaging agents for a serotonin receptor. Compositions comprising an imaging-effective amount of a Radiolabeled Compound are also disclosed.

BACKGROUND OF THE INVENTION

Powerful imaging methods currently exist which enable one to assess the living brain and body in vivo and thereby monitor the effectiveness of treatments that affect brain chemistry and function. Positron Emission Tomography (PET) and Single Photon Emission Computed Tomography (SPECT) are dynamic, non-invasive imaging techniques used in nuclear medicine to study various biochemical and biological process in vivo. In these technologies, radiolabeled compounds may be administered in nanomolar or picomolar concentrations, allowing imaging studies to be performed without perturbing the biological system being studied. These labeled compounds may generally be radioisotopes that give off positrons. The emitted positrons may then collide with electrons, which generate gamma rays. The emitted gamma rays may then be detected by scanners and be processed to obtain images of the living brain and body. Like other dynamic imaging protocols, PET and SPECT have the ability collect images repeatedly over time and provide information about regional distribution of the tracer as well as the change in compartmental distribution as a function of time. As such, PET and SPECT lend themselves directly to measuring kinetic processes, such as rate of tracer uptake by cells, substrate metabolic rates, receptor density/affinity, and regional blood flow.

The serotonin (5-hydroxytryptamine; 5-HT) system in the brain is an important neurotransmission network regulating various physiological functions and behavior including anxiety and mood states. Serotonin has been linked with major depression, bipolar disorder, eating disorders, alcoholism, pain, anxiety, obsessive-compulsive disorders, Alzheimer's Disease, Parkinson's disease and other psychiatric maladies. It is also involved in mediating the action of many psychotropic drugs including antidepressants, anti-anxiety drugs and anti-psychotics. There are more than a dozen known subtypes of serotonin receptors. Among these serotonin receptors, the 5-HT$_{1A}$ receptor plays a role as a pre-synaptic autoreceptor in the dorsal raphe nucleus and as a postsynaptic receptor for serotonin in terminal field areas.

Several radioligands for 5-HT$_{1A}$ receptors have been prepared and evaluated. The most successful radioligands studied so far for 5-HT$_{1A}$ receptors are antagonist tracers which bind with both the G-protein-coupled high affinity (HA) state and uncoupled low affinity (LA) state of 5-HT$_{1A}$ receptors. In contrast, agonists bind preferentially to the HA state of the 5-HT$_{1A}$ receptor. Therefore, having a radioligand agonist tracer may provide a more meaningful functional measure of 5-HT$_{1A}$ receptors.

5-HT$_{1A}$ agonist radiotracers using carbon radioisotopes have been reported. One of the major impediments to using this technology in the clinic is the limited number of centers that can produce C-11 labeled radiotracers. The F-18 tracer can be shipped to multiple centers that are within a radius of 4 hours from the production site. Thus, there is still a need in the art for improved radiolabeled serotonin agonist modulators that are highly selective for imaging 5-HT$_{1A}$ receptors. Moreover, there remains a need in the art for selective radioactive tracers, which are useful for imaging 5-HT$_{1A}$ receptors in vivo. The present invention addresses these needs.

SUMMARY OF THE INVENTION

In one aspect, the present invention provides Radiolabeled Compounds having the Formula (I):

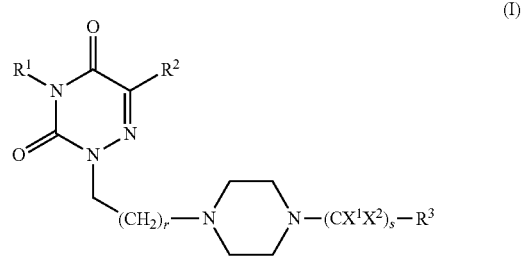

(I)

or a pharmaceutically acceptable salt thereof,
wherein:
r and s are each independently an integer ranging from 0 to 10;

$R^1$ is H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, or 3- to 7-membered heterocycle; each of which can be substituted or unsubstituted, and each of which or its substituents are optionally labeled with $^{11}C$, $^{18}F$, $^{75}Br$, $^{76}Br$, $^{120}I$, $^{123}I$, $^{124}I$, $^{125}I$, $^{131}I$, or $^3H$;

$R^2$ is H, aryl, aralkyl, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, 3- to 7-membered heterocycle, halo, $C_1$-$C_6$ haloalkyl, $N(R^4)_2$, CN, $OR^4$ or $SR^4$; each of which can be substituted or unsubstituted, and each of which and/or its substituents are optionally labeled with $^{11}C$, $^{18}F$, $^{75}Br$, $^{76}Br$, $^{120}I$, $^{123}I$, $^{124}I$, $^{125}I$, $^{131}I$, or $^3H$;

$X^1$ and $X^2$ are independently selected from a single bond, H, $C_1$-$C_6$ alkyl, $C_1$-$C_6$ and haloalkyl; or, $X^1$ and $X^2$ together are imino, oxo, or thioxo;

$R^3$ is aryl or 5- to 7-membered aromatic heterocycle, each of which is substituted with one $R^6$ group and optionally substituted with one or more of the following groups: $C_1$-$C_6$ alkyl, $C_3$-$C_7$ cycloalkyl, $C_3$-$C_7$ cycloalkenyl or 3- to 7-membered heterocycle, halo, $C_1$-$C_6$ haloalkyl, $C_2$-$C_6$ alkenyl, $C_2$-$C_6$ alkynyl, ($C_1$-$C_6$ alkylene)-aryl, $N(R^4)_2$, CN, $OR^4$, $SR^4$, S(O)—$R^4$, $SO_2$—$R^4$, $SO_2NH$—$R^4$, $SO_3H$, NH—$SO_2$—$R^4$, $C(O)R^5$ or $NHC(O)R^5$;

each occurrence of $R^4$ is independently H, $C_1$-$C_6$ alkyl, $C_1$-$C_6$ fluoroalkyl, $C_2$-$C_6$ alkenyl, $C_2$-$C_6$ alkynyl, aryl, ($C_1$-$C_6$ alkylene)-aryl, $C_3$-$C_7$ cycloalkyl, $C_3$-$C_7$ cycloalkenyl or 3- to 7-membered heterocycle;

$R^5$ is $R^4$, $N(R^4)_2$ or $OR^4$;

$R^6$ is L-M;

L is a single bond, O, S, NH, $NR^4$, or, where M is absent, L is selected from F, $^{18}$F, $CF_3$, $CF_2{}^{18}F$, $^{11}CF_3$, $^{11}CF_2H$, $CF_2{}^3H$, CN, $^{11}$CN, $^{75}$Br, $^{76}$Br, $^{120}$I, $^{123}$I, $^{124}$I, $^{125}$I, $^{131}$I, and —$OC^3HH_2$; and M is absent, H, Br, I, $C_1$-$C_6$ alkylene, $C_2$-$C_6$ alkenylene, $C_2$-$C_6$ alkynylene, benzene, pyridine, quinoline, isoquinoline, thiazole, pyrazole, imidazole, biphenyl, naphthalene, isoxazole, furan, thiophene, oxazole, pyrrole, xanthone, anthrone, pyridazine, pyrimidine, pyrazine, indole, isoindole, indazole, purine, or quinazoline; each of which can be substituted or unsubstituted, such as H or aryl, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H.

In another aspect, the present invention provides Radiolabeled Compounds having the Formula (II):

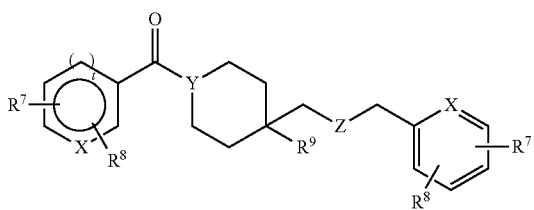

(II)

or a pharmaceutically acceptable salt thereof, wherein:

each $R^7$ is independently —H, -halo, —$C_1$-$C_6$ alkyl, —$C_1$-$C_6$ fluoroalkyl, —$C_3$-$C_7$ cycloalkyl, —$C_3$-$C_7$ cycloalkenyl, $C_2$-$C_6$ alkenyl, —$C_2$-$C_6$ alkynyl, —$N(R^{10})_2$, —CN, —$OR^{10}$, —$SR^{10}$, —S(O)—$R^{10}$, —$SO_2$—$R^{10}$, —$SO_2NH$—$R^{10}$, —$SO_3H$, —NH—$SO_2$—$R^{10}$, —$C(O)R^{11}$, $NHC(O)R^{11}$, -aryl, -3- to 7-membered heterocycle, -alkoxycarbonyl, benzene, pyridine, quinoline, isoquinoline, thiazole, pyrazole, imidazole, biphenyl, naphthalene, isoxazole, furan, thiophene, oxazole, pyrrole, xanthone, anthrone, pyridazine, pyrimidine, pyrazine, indole, isoindole, indazole, purine, quinazoline, or

each of which are optionally substituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H;

each $R^8$ is independently —$Z^a$—$R^{12}$, —H, -halo, —$C_1$-$C_6$ alkyl, -fluoroalkyl, —$C_3$-$C_7$ cycloalkyl, —$C_3$-$C_7$ cycloalkenyl, —$C_2$-$C_6$ alkenyl, alkynyl, —$N(R^{10})_2$, —CN, —$OR^{10}$, —$SR^4$, —S(O)—$R^{10}$, —$SO_2$—$R^{10}$, —$SO_2NH$—$R^{10}$, —$SO_3H$, —NH—$SO_2$—$R^{10}$, —$C(O)R^{11}$, —$NHC(O)R^{11}$, -aryl, -3- to 7-membered heterocycle, -alkoxycarbonyl, benzene, pyridine, quinoline, isoquinoline, thiazole, pyrazole, imidazole, biphenyl, naphthalene, isoxazole, furan, thiophene, oxazole, pyrrole, xanthone, anthrone, pyridazine, pyrimidine, pyrazine, indole, isoindole, indazole, purine, quinazoline, or

each of which are optionally substituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H;

$R^9$ is H, F, Br, I, $^3$H, $^{18}$F, $^{75}$Br, $^{76}$Br, $^{120}$I, $^{123}$I, $^{124}$I, $^{125}$I, or $^{131}$I;

each $R^{10}$ is independently —H, —$C_1$-$C_6$ alkyl, —$C_1$-$C_6$ fluoroalkyl, —$C_2$-$C_6$ alkenyl, $C_2$-$C_6$ alkynyl, -aryl, —($C_1$-$C_6$ alkylene)-aryl, —$C_3$-$C_7$ cycloalkyl, —$C_3$-$C_7$ cycloalkenyl or -3- to 7-membered heterocycle;

$R^{11}$ is —$R^4$, —$N(R^4)_2$ or —$OR^4$;

$R^{12}$ is —$C_1$-$C_6$ alkyl, —$C_2$-$C_6$ alkenyl, alkynyl, $C_1$-$C_6$ alkylene)-aryl, —($C_2$-$C_6$ alkenylene)-aryl, $C_2$-$C_6$ alkynylene)-aryl, benzene, pyridine, quinoline, isoquinoline, thiazole, pyrazole, imidazole, biphenyl, naphthalene, isoxazole, furan, thiophene, oxazole, pyrrole, xanthone, anthrone, pyridazine, pyrimidine, pyrazine, indole, isoindole, indazole, purine, or quinazoline; each of which are optionally substituted, and each of which and/or its substituents are optionally labeled with $^{11}$C, $^{18}$F, $^{75}$Br, $^{76}$Br, $^{120}$I, $^{123}$I, $^{124}$I, $^{125}$I, $^{131}$I, or $^3$H;

each X is independently —CH—, —N—, —S—, or —O—;

Y is —CH— or —N—;

Z is —$CH_2$—, —NH, —S—, or —O—

$Z^a$ is —O—, —S—, or —NH—;

t is 0 or 1, such that t is zero when X is —S— or —O—; and u is 1 or 2.

The Compounds of Formula (I) and Formula (II) (the "Radiolabeled Compounds") are useful for: (i) detecting in vivo 5-$HT_{1A}$ receptors in a subject; (ii) treating or preventing a psychiatric disorder in a subject, and/or (iii) stabilizing the mood of a subject having a mood disorder.

In yet another aspect, the present invention provides a method for detecting in vivo 5-$HT_{1A}$ receptors in a subject, the method comprising:

(a) administering to the subject an imaging-effective amount of a Radiolabeled Compound or a pharmaceutically acceptable salt thereof, and (b) detecting the radioactive emission of the compound or salt thereof administered to the subject.

In the present methods, the radioactive emissions from the labeled isotopes of a Radiolabeled Compound can be detected using techniques for imaging 5-$HT_{1A}$ receptors in a subject. The radioactive emission can be detected anywhere in the body of the subject. In one embodiment, the radioactive emission is detected in the brain of the subject.

The radiolabeled compounds are useful for diagnosing, and/or evaluating a psychiatric or neurological disorder in a subject, and/or measuring the occupancy of the receptor by specific treatments or the effect on the receptor of specific treatments or prediction of treatment response. In a further embodiment, the subject can be known or suspected to have a psychiatric or neurological disorder.

The invention also relates to compositions comprising a physiologically acceptable carrier or vehicle and an amount of a Radiolabeled Compound that is effective to: (i) diagnose, and/or evaluate a psychiatric disorder or neurological disorder in a subject; and/or (ii) measure the occupancy of the receptor by specific treatments or the effect on the receptor of specific treatments or prediction of treatment response. The compositions are able to do this because they are able to detect in vivo 5-$HT_{1A}$ receptors in a subject. The compositions are also useful for evaluating potential new treatments for depression, anxiety disorders, various neurological and other disorders whose pathophysiology involves this receptor or where the treatment affects or targets this receptor.

The present invention may be understood more fully by reference to the following detailed description and illustrative examples, which are intended to exemplify non-limiting embodiments of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Definitions and Abbreviations

Figure 1:
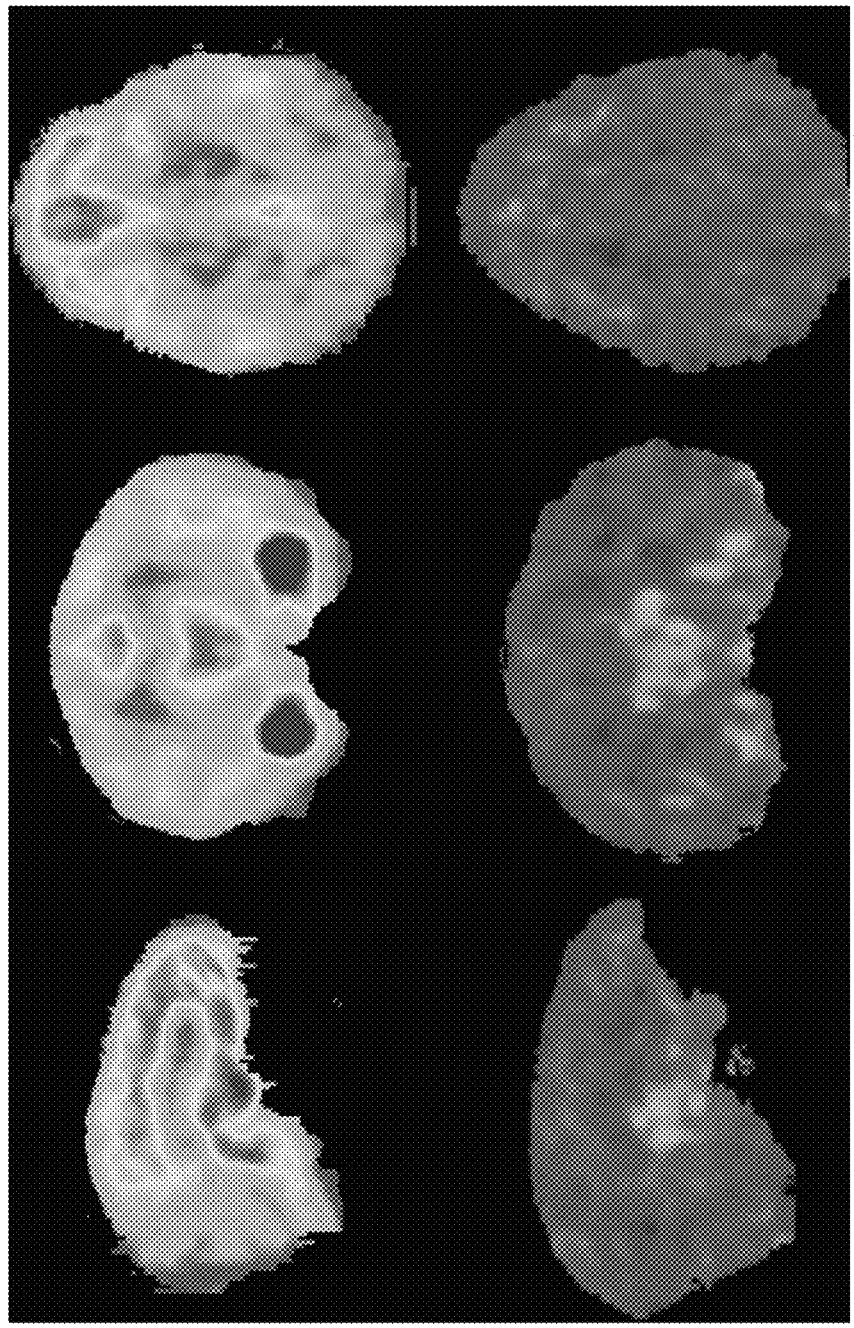
FIG. 1: Sum of 60-180 minute of Compound F image in baboon. $1^{st}$ row: Base line; $2^{nd}$ row: Chase with WAY100635. First column: sagittal, middle column: coronal, last column: axial views.

The terms used herein having following meanings:

The term "alkyl" as used herein, refers to a straight chain or branched non-cyclic hydrocarbon, wherein one of the hydrocarbon's hydrogen atoms has been replaced with a single bond. Hence, the term "$C_1$-$C_6$ alkyl" as used herein, refers to a straight chain or branched non-cyclic hydrocarbon having from 1 to 6 carbon atoms, wherein one of the hydrocarbon's hydrogen atoms has been replaced with a single bond. Representative straight chain $C_1$-$C_6$ alkyls include methyl, ethyl, n-propyl, n-butyl, n-pentyl, and n-hexyl. Representative branched $C_1$-$C_6$ alkyls include isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, neohexyl, isohexyl, and the like. In certain embodiments, the $C_1$-$C_6$ alkyl may be substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "haloalkyl" as used herein, refers to a $C_1$-$C_6$ alkyl group wherein one or more of the $C_1$-$C_6$ alkyl group's hydrogen atoms have been replaced with a halogen atom. Representative halogen atoms include fluorine, bromine and iodine. Representative fluoroalkyls include monofluoromethyl —$CHF_2$, —$CH_2F$, —$CF_3$, —$CH(F)CH_3$, or —$CF_2CH_3$. In certain embodiments, the haloalkyl may be substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "alkenyl" as used herein, refers to a straight chain or branched non-cyclic hydrocarbon including at least one carbon-carbon double bond, wherein one of the hydrocarbon's hydrogen atoms has been replaced with a single bond. Hence, the term "$C_2$-$C_6$ alkenyl" as used herein, refers to a straight chain or branched non-cyclic hydrocarbon having from 2 to 6 carbon atoms and including at least one carbon-carbon double bond, wherein one of the hydrocarbon's hydrogen atoms has been replaced with a single bond. Representative straight chain and branched $C_2$-$C_6$ alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, and the like. In certain embodiments, the $C_2$-$C_6$ alkenyl may be substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "alkynyl" as used herein, refers to a straight chain or branched non-cyclic hydrocarbon including at lease one carbon-carbon triple bond, wherein one of the hydrocarbon's hydrogen atoms has been replaced with a single bond. Hence, the term "$C_2$-$C_6$ alkynyl" as used herein, refers to a straight chain or branched non-cyclic hydrocarbon having from 2 to 6 carbon atoms and including at lease one carbon-carbon triple bond, wherein one of the hydrocarbon's hydrogen atoms has been replaced with a single bond. Representative straight chain and branched $C_2$-$C_6$ alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, and the like. In certain embodiments, the $C_2$-$C_6$ alkynyl may be substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "alkylene" as used herein, refers to a straight chain or branched non-cyclic hydrocarbon, wherein two of the hydrocarbon's hydrogen atoms have been replaced with a single bond. Hence, the term "$C_1$-$C_6$ alkylene" as used herein, refers to a straight chain or branched non-cyclic hydrocarbon having from 1 to 6 carbon atoms, wherein two of the hydrocarbon's hydrogen atoms have been replaced with a single bond.

A "$^{11}$C-labeled $C_1$-$C_6$ alkylene group" is a $C_1$-$C_6$ alkylene group, as defined above, wherein one of the $C_1$-$C_6$ alkylene group's carbon atoms has been replaced with a $^{11}$C isotope.

A "$^{11}$C-labeled $C_1$-$C_6$ alkyl group" is a $C_1$-$C_6$ alkyl group, as defined above, wherein one of the $C_1$-$C_6$ alkyl group's carbon atoms has been replaced with a $^{11}$C isotope. Representative $^{11}$C-labeled $C_1$-$C_6$ alkylene groups include, but are not limited to, $^{11}CH_2$, $CH_2{}^{11}CH_2$, $CH_2CH_2{}^{11}CH_2$, $CH_2CH_2CH_2{}^{11}CH_2$, $CH_2CH_2CH_2CH_2{}^{11}CH_2$, and $CH_2CH_2CH_2CH_2CH_2{}^{11}CH_2$.

A "$^{18}$F-labeled $C_1$-$C_6$ alkylene group" is a $C_1$-$C_6$ alkyl group, as defined above, wherein one of the $C_1$-$C_6$ alkyl group's hydrogen atoms has been replaced with a $^{18}$F isotope.

The term "alkenylene" as used herein, refers to a straight chain or branched non-cyclic hydrocarbon including at least one carbon-carbon double bond, wherein two of the hydrocarbon's hydrogen atoms have been replaced with a single bond. Hence, the term "$C_2$-$C_6$ alkenylene" as used herein, refers to a straight chain or branched non-cyclic hydrocarbon having from 2 to 6 carbon atoms and including at least one carbon-carbon double bond, wherein two of the hydrocarbon's hydrogen atoms have been replaced with a single bond.

A "$^{11}$C-labeled $C_2$-$C_6$ alkenylene group" is a $C_2$-$C_6$ alkenylene group, as defined above, wherein one of the $C_2$-$C_6$ alkenylene group's carbon atoms has been replaced with a $^{11}$C isotope.

A "$^{18}$F-labeled $C_2$-$C_6$ alkenylene group" is a $C_2$-$C_6$ alkenylene group, as defined above, wherein one of the $C_2$-$C_6$ alkenylene group's hydrogen atoms has been replaced with a $^{18}$F isotope.

The term "alkynylene" as used herein, refers to a straight chain or branched non-cyclic hydrocarbon including at lease one carbon-carbon triple bond, wherein two of the hydrocarbon's hydrogen atoms have been replaced with a single bond. Hence, the term "$C_2$-$C_6$ alkynylene" as used herein, refers to a straight chain or branched non-cyclic hydrocarbon having from 2 to 6 carbon atoms and including at lease one carbon-carbon triple bond, wherein two of the hydrocarbon's hydrogen atoms have been replaced with a single bond.

A "$^{11}$C-labeled $C_2$-$C_6$ alkynylene group" is a $C_2$-$C_6$ alkynylene group, as defined above, wherein one of the $C_2$-$C_6$ alkynylene group's carbon atoms has been replaced with a $^{11}$C isotope.

A "$^{18}$F-labeled $C_2$-$C_6$ alkynylene group" is a $C_2$-$C_6$ alkynylene group, as defined above, wherein one of the $C_2$-$C_6$ alkynylene group's hydrogen atoms has been replaced with a $^{18}$F isotope.

The term "alkoxycarbonyl" means a moiety of the formula —COOR', where R' is unsubstituted $C_1$-$C_6$ alkyl. Examples of such alkoxycarbonyl include methoxycarbonyl, ethoxycarbonyl, and the like.

The term "aryl" as used herein refers to a $C_6$-$C_{14}$ aromatic group. Exemplary aryl groups include a phenyl group, a biphenyl group, biphenylene group, anthracene group, fulvene group, phenanthrene group, or a naphthyl group. In certain embodiments, the aryl group may be substituted with one or more of the following groups: halo, O—$C_1$-$C_6$ alkyl, O—$C_2$-$C_6$ alkenyl, O—$C_2$-$C_6$ alkynyl, OH, CN, COOR', OC(O)R', N(R')$_2$, NHC(O)R', S—($C_1$-$C_6$ alkyl or alkenyl or alkynyl), S—(O)—$C_1$-$C_6$ alkyl, S(O)—$C_2$-$C_6$ alkenyl, S(O)—$C_2$-$C_6$ alkynyl, S—($O_2$)—$C_1$-$C_6$ alkyl, S($O_2$)—$C_2$-$C_6$ alkenyl, S($O_2$)—$C_2$-$C_6$ alkynyl, or C(O)NHR' groups wherein each R' is independently —H or unsubstituted —$C_1$-$C_6$ alkyl.

The term "cycloalkyl" as used herein refers to a saturated non-aromatic monocyclic cycloalkyl ring. Hence, the term "$C_3$-$C_7$ cycloalkyl" as used herein refers to a 3-, 4-, 5-, 6- or 7-membered saturated non-aromatic monocyclic cycloalkyl ring. Representative $C_3$-$C_7$ monocyclic cycloalkyl groups include, but are not limited to, cyclopropyl, cyclobutyl, cyclopentyl, cyclohexyl and cycloheptyl. In certain embodiments, the cylcoalkyl group may be substituted with one or more of the following groups: halo, O—$C_1$-$C_6$ alkyl, O—$C_2$-$C_6$ alkenyl, O—$C_2$-$C_6$ alkynyl, OH, CN, COOR', OC(O)R', N(R')$_2$, NHC(O)R', S—($C_1$-$C_6$ alkyl or alkenyl or alkynyl), S—(O)—$C_1$-$C_6$ alkyl, S(O)—$C_2$-$C_6$ alkenyl, S(O)—$C_2$-$C_6$ alkynyl, S—($O_2$)—$C_1$-$C_6$ alkyl, S($O_2$)—$C_2$-$C_6$ alkenyl, S($O_2$)—$C_2$-$C_6$ alkynyl, or C(O)NHR' groups wherein each R' is independently H or unsubstituted $C_1$-$C_6$ alkyl.

The term "cycloalkenyl" as used herein refers to non-aromatic monocyclic carbocyclic ring having at least one endocyclic double bond. Hence, the term "$C_3$-$C_7$ cycloalkenyl" as used herein refers to a 3-, 4-, 5-, 6- or 7-membered non-aromatic monocyclic carbocyclic ring having at least one endocyclic double bond, but which is not aromatic. It is to be understood that when any two groups, together with the carbon atom to which they are attached form a $C_3$-$C_7$ monocyclic cycloalkenyl group, the carbon atom to which the two groups are attached remain tetravalent. Representative $C_3$-$C_7$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl and -1,3,5-cycloheptatrienyl. In one embodiment, the cycloalkenyl group is substituted with one or more of the following groups: halo, O—$C_1$-$C_6$ alkyl, O—$C_2$-$C_6$ alkenyl, O—$C_2$-$C_6$ alkynyl, OH, CN, COOR', OC(O)R', N(R')$_2$, NHC(O)R', S—($C_1$-$C_6$ alkyl or alkenyl or alkynyl), S—(O)—$C_1$-$C_6$ alkyl, S(O)—$C_2$-$C_6$ alkenyl, S(O)—$C_2$-$C_6$ alkynyl, S—($O_2$)—$C_1$-$C_6$ alkyl, S($O_2$)—$C_2$-$C_6$ alkenyl, S($O_2$)—$C_2$-$C_6$ alkynyl, or C(O)NHR' groups wherein each R' is independently H or unsubstituted $C_1$-$C_6$ alkyl.

The terms "halo" or "halogen" as used herein, refer to F, Cl, Br, or I, or their radioactive isotopes. Exemplary radioactive isotopes include $^{18}$F, $^{75}$Br, $^{76}$Br, $^{120}$I, $^{123}$I, $^{124}$I, $^{125}$I, and $^{131}$I.

The term "3- to 7-membered heterocycle" refers to: (i) a 3- or 4-membered non-aromatic monocyclic cycloalkyl in which one of the ring carbon atoms has been replaced with a N, O or S atom; (ii) a 5-, 6-, or 7-membered aromatic or non-aromatic monocyclic cycloalkyl in which 1-4 of the ring carbon atoms have been independently replaced with a N, O or S atom. The term 3- to 7-membered heterocycle also encompasses any heterocycles described by (i) or (ii) which are fused to a benzene ring, or in which any one of the ring carbon atoms comprises a carbonyl group, such as in lactam and lactone ring systems. The non-aromatic 3- to 7-membered heterocycles can be attached via a ring nitrogen, sulfur, or carbon atom. The aromatic 3- to 7-membered heterocycles are attached via a ring carbon atom. Representative examples of a 3- to 7-membered heterocycle group include, but are not limited to, dihydrofuran-2-one, dihydrofuranyl, furanyl, benzofuranyl, furazanyl, imidazolidinyl, imidazolinyl, imidazolyl, benzimidazolyl, indazolyl, indolinyl, indolyl, indolizinyl, isoindolinyl, isothiazolyl, isoxazolyl, benzisoxazolyl, morpholinyl, oxadiazolyl, oxazolidinyl, oxazolyl, benzoxazolyl, oxazolidinyl, pyrimidinyl, phenanthridinyl, phenanthrolinyl, piperazinyl, piperidinyl, pyranyl, benzopyranyl, pyrazinyl, pyrazolidinyl, pyrazolinyl, pyrazolyl, pyridazinyl, pyridooxazole, pyridoimidazole, pyridothiazole, pyridyl, pyrimidinyl, pyrrolidinyl, pyrrolinyl, quinolinyl, isoquinolinyl, quinoxalinyl, phthalazinyl, cinnolinyl, quinolizinyl, quinazolinyl, quinuclidinyl, tetrahydrofuranyl, thiadiazinyl, thiadiazolyl, thiazolyl, benzthiazolyl, thienyl, thienothiazolyl, thienooxazolyl, thienoimidazolyl, thiomorpholinyl, thiophenyl, benzothiphenyl, triazinyl, and triazolyl. In one embodiment, the 3- to 7-membered heterocycle group is substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "5- to 7-membered aromatic heterocycle" refers to a 5-, 6-, or 7-membered aromatic monocyclic cycloalkyl in which 1-4 of the ring carbon atoms have been independently replaced with a N, O or S atom. The term 5- to 7-membered aromatic heterocycle also encompasses any heterocycles described which are fused to a benzene ring, or in which any one of the ring carbon atoms comprises a carbonyl group, such as in lactam and lactone ring systems. The 5- to 7-membered aromatic heterocycles are attached via a ring carbon atom. Representative examples of a 5- to 7-membered aromatic heterocycle group include, but are not limited to, furanyl, benzofuranyl, furazanyl, imidazolyl, benzimidazolyl, indazolyl, indolyl, indolizinyl, isoindolinyl, isothiazolyl, isoxazolyl, benzisoxazolyl, oxadiazolyl, oxazolidinyl, oxazolyl, benzoxazolyl, oxazolidinyl, pyrimidinyl, phenanthridinyl, phenanthrolinyl, pyranyl, benzopyranyl, pyrazinyl, pyrazolyl, pyridazinyl, pyridooxazole, pyridoimidazole, pyridothiazole, pyridyl, pyrimidinyl, quinolinyl, isoquinolinyl, quinoxalinyl, phthalazinyl, cinnolinyl, quinolizinyl, quinazolinyl, thiadiazinyl, thiadiazolyl, thiazolyl, benzthiazolyl, thienyl, thienothiazolyl, thienooxazolyl, thienoimidazolyl, thiophenyl, and benzothiphenyl. In certain embodiments, the 5- to 7-membered aromatic heterocycle group may be substituted with one or more of the following groups: halo, O—($C_1$-$C_6$ alkyl), OH, CN, COOR', OC(O)R', N(R')$_2$, NHC(O)R' or C(O)NHR' groups wherein each R' is independently H or unsubstituted $C_1$-$C_6$ alkyl.

The term "imaging-effective amount" when used in connection with a Radiolabeled Compound of the present invention or pharmaceutically acceptable salt thereof, is an amount of the compound that is sufficient to produce a visible image when the compound is administered to a subject and the radiation emitted by the compound is detected using positron-emission tomography ("PET") or single photon emission tomography (SPECT) or autoradiography or ex vivo or in vitro binding assays.

The term "isolated" as used herein means separate from other components of a reaction mixture or natural source. In certain embodiments, the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of a Radiolabeled Compound of the present invention by weight of the isolate. In one embodiment, the isolate contains at least 95% of a Radiolabeled Compound of the present invention by weight of the isolate.

The phrase "pharmaceutically acceptable salt," as used herein, is a salt of an acid and a basic nitrogen group of a Radiolabeled Compound of the present invention. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt of a Radiolabeled Compound of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as tri-(2-hydroxyethyl) amine or N,N-dimethyl-N-(2-hydroxyethyl)amine; N-methyl-D-glucamine; or amino acids such as arginine, lysine, and the like. The term "pharmaceutically acceptable salt" also includes a hydrate of a Radiolabeled Compound of the present invention.

As used herein, a "5-$HT_{1A}$ selective agent" refers to a compound that can selectively interact with the 5-$HT_{1A}$ receptor relative to the other known transporters, receptors, enzymes and proteins. 5-$HT_{1A}$ selective agents include agonists and antagonists that specifically or preferentially bind to 5-$HT_{1A}$ receptors.

The term "subject," as used herein, includes, but is not limited to, a non-human animal, such as a cow, monkey, chimpanzee, baboon, horse, sheep, pig, chicken, turkey, quail, cat, dog, mouse, rat, rabbit, or guinea pig; and a human. In one embodiment, a monkey is a rhesus. In another embodiment, a subject is a baboon. In another embodiment, a subject is a human.

The term "therapeutically effective amount" when used in connection with a Radiolabeled Compound of the present invention or a pharmaceutically acceptable salt thereof is an amount that is effective to (i) treat or prevent a psychiatric or neurological disorder in a subject, or (ii) stabilize the mood of a subject having a mood disorder.

The following abbreviations are used herein and have the indicated definitions: n-BuOH is n-butyl alcohol; DMSO is N,N-dimethylsulfoxide; EtOH is ethanol; Et$_3$N is triethylamine; Kryptofix® 222 is 4,7,13,16,21,24-hexaoxa-1,10-diazabicyclo[8.8.8]-hexacosane (Acros Organics, Belgium); mCPBA is m-chloroperbenzoic acid; MeNH$_2$ is methylamine; Ms or mesyl is methanesulfonyl; MS is mass spectrometry; NMR is nuclear magnetic resonance; PEG is polyethylene glycol; py is pyridine; TBAH is tetrabutylammonium hydroxide; Ts or tosyl is -p-toluenesulfonyl; TsCl is p-toluenesulfonyl chloride; Tf or triflyl is trifluoromethanesulfonate; TMSCN is trimethylsilylcyanide; NaI is sodium iodide; (Bu)$_3$Sn is tributyl tin or tributylstannyl; (Me)$_3$Sn is trimethyl tin or trimethylstannyl; NBS is N-bromosuccinimide; BF$_3$K is potassium trifluoroborane.

The Radiolabeled Compounds

The Radiolabeled Compounds of the present invention may be useful as imaging agents for one or more 5-$HT_{1A}$ receptors.

In certain embodiments, the Radiolabeled Compounds of the present invention may have one or more of the following characteristics: (i) high affinity and selectivity for the 5-$HT_{1A}$ receptor compared to the other known transporters, receptors, enzymes and proteins; (ii) sufficient lipophilicity to allow rapid blood-brain-barrier penetration and generation of polar metabolites that do not cross the blood-brain-barrier; and (iii) high specific activity of the radiolabeled groups of the compounds of the present invention.

It is possible for the Radiolabeled Compounds of the present invention to have one or more chiral centers, and, as such, the Radiolabeled Compounds can exist in various stereoisomeric forms. Accordingly, Formula (I) and Formula (II), although not depicting specific stereoisomers of the Radiolabeled Compounds, are understood to encompass all possible stereoisomers including, for example, tautomeric forms, diastereomers, enantiomers, and cis/trans-isomers. Also included within the scope of the invention are polymorphs, amorphous forms, solvates and hydrates of the compounds of the invention.

The Radiolabeled Compounds of Formula (I)

As stated above, the Radiolabeled Compounds having the Formula (I):

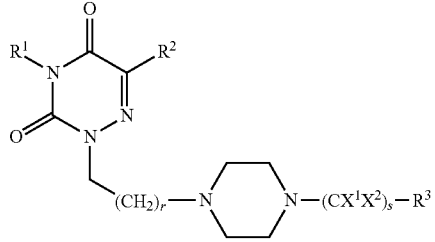

or pharmaceutically acceptable salts thereof, wherein $R^1$, $R^2$, $R^3$, $X^1$, $X^2$, r and s are as defined above for the Radiolabeled Compounds of Formula (I) are described.

In one embodiment, the compound of formula (I) comprises at least one radioactive element, or radiolabel. In one embodiment, the compound of formula (I) comprises one radioactive element, or radiolabel.

In one embodiment, the radiolabel is selected from the group consisting of a radioactive isotope of hydrogen, carbon and a halogen. In another embodiment, the radiolabel is selected from the group consisting of $^3H$, $^{11}C$, $^{18}F$, $^{75}Br$, $^{76}Br$, $^{120}I$, $^{123}I$, $^{124}I$, $^{125}I$ and $^{131}I$. In one embodiment, the radiolabel is $^3H$, $^{11}C$, or $^{18}F$. In one embodiment, the radiolabel is $^3H$, $^{75}Br$, $^{76}Br$, $^{120}I$, $^{123}I$, $^{124}I$, $^{125}I$ or $^{131}I$. In one embodiment, the radiolabel is $^{75}Br$, $^{76}Br$, $^{120}I$, $^{123}I$, $^{124}I$, $^{125}I$ or $^{131}I$. In another embodiment, the radiolabel is $^{18}F$.

In one embodiment, $R^1$ is $C_1$-$C_6$ alkyl.
In another embodiment, $R^1$ is ethyl.
In another embodiment, $R^1$ is methyl.
In one embodiment, $R^2$ is $C_1$-$C_6$ alkyl.
In one embodiment, $R^2$ is H.
In another embodiment, $R^2$ is H, and $R^1$ is methyl.
In one embodiment, $R^3$ is aryl.
In still another embodiment, $R^3$ is aryl substituted with a radioactive isotope of fluorine, bromine, iodine, or hydrogen, such as $^{18}F$, $^{75}Br$, $^{76}Br$, $^{120}I$, $^{123}I$, $^{124}I$, $^{125}I$, $^{131}I$, and —$OC^3HH_2$.
In still another embodiment, $R^3$ is aryl substituted with a radioactive isotope of bromine, iodine, or hydrogen, such as $^{75}Br$, $^{76}Br$, $^{120}I$, $^{123}I$, $^{124}I$, $^{125}I$, $^{131}I$, and —$OC^3HH_2$.
In still another embodiment, $R^3$ is phenyl substituted with a radioactive isotope of bromine, iodine, or hydrogen, such as $^{75}Br$, $^{76}Br$, $^{120}I$, $^{123}I$, $^{124}I$, $^{125}I$, $^{131}I$, and —$OC^3HH_2$.
In still another embodiment, $R^3$ is phenyl substituted with $^{75}Br$, $^{76}Br$, $^{120}I$, $^{123}I$, $^{124}I$, $^{125}I$, $^{131}I$, or —$OC^3HH_2$.
In still another embodiment, $R^3$ is phenyl substituted with —$OC^3HH_2$. In still another embodiment, $R^3$ is phenyl substituted with —$OC^3HH_2$.
In another embodiment, $R^3$ is naphthyl.
In still another embodiment, $R^3$ is naphthyl substituted with a radioactive isotope of fluorine, bromine, iodine, or hydrogen, such as $^{18}F$, $^{75}Br$, $^{76}Br$, $^{120}I$, $^{123}I$, $^{124}I$, $^{125}I$, $^{131}I$, and —$OC^3HH_2$.
In still another embodiment, $R^3$ is naphthyl substituted with a radioactive isotope of bromine, iodine, or hydrogen, such as $^{75}Br$, $^{76}Br$, $^{120}I$, $^{123}I$, $^{124}I$, $^{125}I$, $^{131}I$, and —$OC^3HH_2$.
In yet another embodiment, $R^3$ is aryl or 5- to 7-membered aromatic heterocycle, each of which are optionally substituted with one $R^6$ group.

In one embodiment, $R^6$ is selected from —$C_1$-$C_6$ alkylene, —$C_2$-$C_6$ alkenylene, —$C_2$-$C_6$ alkynylene, —O—$C_1$-$C_6$ alkylene, —S—$C_1$-$C_6$ alkylene, —NH—$C_1$-$C_6$ alkylene, and —$NR^4$—$C_1$-$C_6$ alkylene, each of which are optionally labeled with a radioactive isotope of fluorine, carbon, bromine, iodine or hydrogen.

In one embodiment, $R^6$ is —O—$C_1$-$C_6$ alkylene labeled with a radioactive isotope of fluorine, carbon, bromine, iodine or hydrogen.

In one embodiment, $R^6$ is —O—$C_1$-$C_3$ alkylene labeled with a radioactive isotope of fluorine, carbon, bromine, iodine or hydrogen.

In one embodiment, $R^6$ is —O—$C_1$-$C_3$ alkylene labeled with a radioactive isotope of fluorine.

In another embodiment, $R^6$ is $OCH_2CH_2CH_2^{18}F$. In still another embodiment, $R^6$ is $OCH_2CH_2^{18}F$.

In one embodiment, r is 3.
In another embodiment, s is 0.
In still another embodiment, r is 3 and s is 0.
In one embodiment, $X^1$ is H, —$C_1$-$C_6$ alkyl, or —$C_1$-$C_6$ haloalkyl.
In another embodiment, $X^1$ is H.
In yet another embodiment, $X^1$ and $X^2$ are H.
In yet another embodiment, $R^3$ is naphthyl substituted with a radioactive isotope of fluorine, bromine, iodine, or hydrogen, such as $^{18}F$, $^{75}Br$, $^{76}Br$, $^{120}I$, $^{123}I$, $^{124}I$, $^{125}I$, $^{131}I$, and —$OC^3HH_2$, r is 3, and s is 0.
In yet another embodiment, $R^3$ is aryl substituted with a radioactive isotope of fluorine, bromine, iodine, or hydrogen, such as $^{18}F$, $^{75}Br$, $^{76}Br$, $^{120}I$, $^{123}I$, $^{124}I$, $^{125}I$, $^{131}I$, and —$OC^3HH_2$, r is 3, and s is 0.

In certain embodiments, Radiolabeled Compounds having the Formula (Ia):

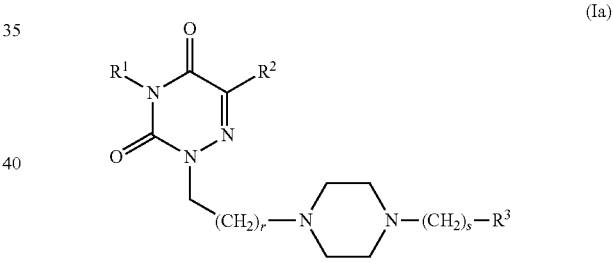

or a pharmaceutically acceptable salts thereof, are described, wherein:
r and s are each independently an integer ranging from 0 to 3;
$R^1$ is —$C_1$-$C_6$ alkyl,
$R^2$ is —H, and
$R^3$ is -aryl or -napththyl, each of which is substituted with $^{75}Br$, $^{76}Br$, $^{120}I$, $^{123}I$, $^{124}I$, $^{125}I$, $^{131}I$, or —$OC^3HH_2$.

In certain embodiments, Radiolabeled Compounds having the Formula (Ib)

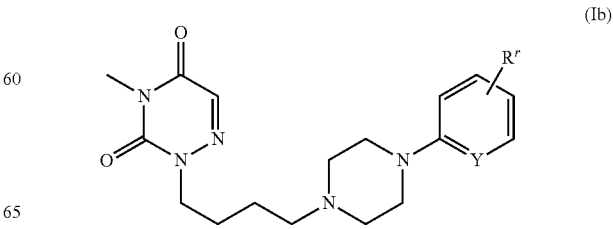

or pharmaceutically acceptable salts thereof are described, wherein Y is —CH— or —N— and $R^r$ is —$C_1$-$C_6$ alkylene, —$C_2$-$C_6$ alkenylene, —$C_2$-$C_6$ alkynylene, —O—$C_1$-$C_6$ alkylene, —S—$C_1$-$C_6$ alkylene, —NH—$C_1$-$C_6$ alkylene, or —$NR^4$—$C_1$-$C_6$ alkylene, each of which are labeled with a radioactive isotope of fluorine, carbon, bromine, iodine or hydrogen; or $R^r$ is a radioactive isotope of F, Br, I, such as $^{18}F$, $^{75}Br$, $^{76}Br$, $^{120}I$, $^{123}I$, $^{124}I$, or $^{125}I$.

In certain embodiments, Radiolabeled Compounds having the Formula (Ib)

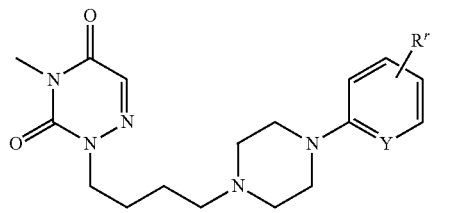

(Ia)

or pharmaceutically acceptable salts thereof is described, wherein Y is —CH— or —N— and $R^r$ is —$OC^3HH_2$ or a radioactive isotope of Br, I, such as $^{75}Br$, $^{76}Br$, $^{120}I$, $^{123}I$, $^{124}I$, or $^{125}I$.

Illustrative Radiolabeled Compounds of Formula (I), (Ia) or (Ib) include the compounds having the structure:

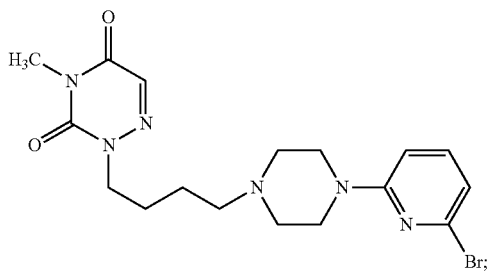 [SMILES: Cn1c(=O)cnn(CCCCN2CCN(c3cccc(Br)n3)CC2)c1=O]

A

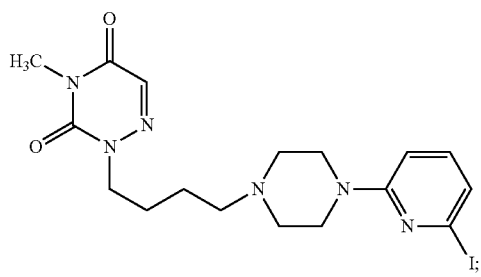 [SMILES: Cn1c(=O)cnn(CCCCN2CCN(c3cccc(I)n3)CC2)c1=O]

B

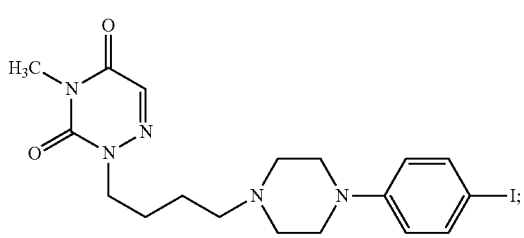 [SMILES: Cn1c(=O)cnn(CCCCN2CCN(c3ccc(I)cc3)CC2)c1=O]

C

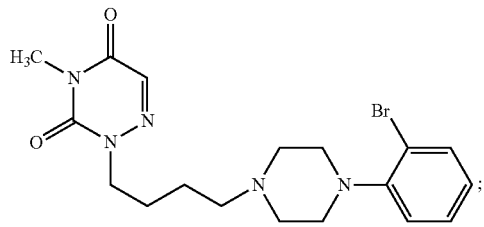 [SMILES: Cn1c(=O)cnn(CCCCN2CCN(c3ccccc3Br)CC2)c1=O]

D

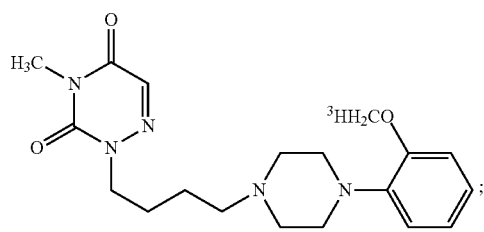

E and pharmaceutically acceptable salts thereof, wherein Br can be $^{75}Br$ or $^{76}Br$ and I can be $^{120}I$, $^{123}I$, $^{124}I$, $^{125}I$, or $^{131}I$.

In certain embodiments, Radiolabeled Compounds having the Formula (Ic):

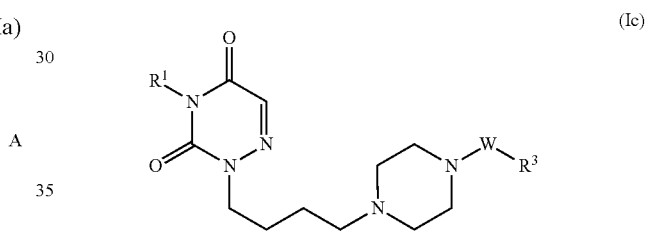

(Ic)

or a pharmaceutically acceptable salts thereof, are described, wherein:

$R^1$ is —$C_1$-$C_6$ alkyl,

W is a bond or a carbonyl; and $R^3$ is -aryl or -heteroaryl, each of which are optionally substituted with $^{18}F$, or —O—$C_1$-$C_4$alkyl, wherein —O—$C_1$-$C_4$alkyl is further substituted with $^{18}F$; and wherein said aryl or heteroaryl are optionally substituted with —CN.

In certain embodiments of Radiolabeled Compounds having the Formula (Ic), W is a bond.

In certain embodiments of Radiolabeled Compounds having the Formula (Ic), $R^3$ is -aryl substituted with —O—$CH_2$—$^{18}F$, —O—$CH_2$—$CH_2$—$^{18}F$, or —O—$CH_2$—$CH_2$—$CH_2$—$^{18}F$.

In certain embodiments of Radiolabeled Compounds having the Formula (Ic), W is a bond and $R^3$ is -aryl substituted with —O—$CH_2$—$^{18}F$, —O—$CH_2$—$CH_2$—$^{18}F$, or —O—$CH_2$—$CH_2$—$CH_2$—$^{18}F$.

In certain embodiments of Radiolabeled Compounds having the Formula (Ic), W is a bond and $R^3$ is phenyl or naphthyl, wherein phenyl or naphthyl are substituted with —O—$CH_2$—$^{18}F$, —O—$CH_2$—$CH_2$—$^{18}F$, or —O—$CH_2$—$CH_2$—$CH_2$—$^{18}F$.

In certain embodiments of Radiolabeled Compounds having the Formula (Ic), W is a bond and $R^3$ is phenyl substituted with —O—$CH_2$—$CH_2$—$^{18}F$.

In one embodiment, Radiolabeled Compounds of Formula (Ic) include:
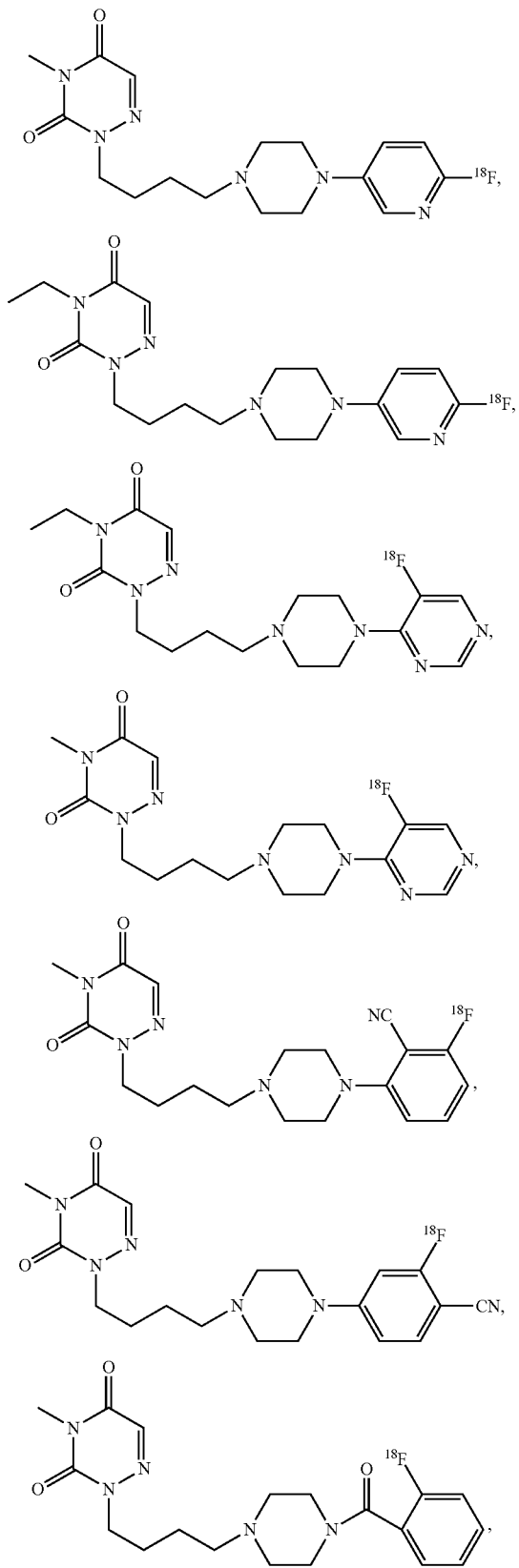
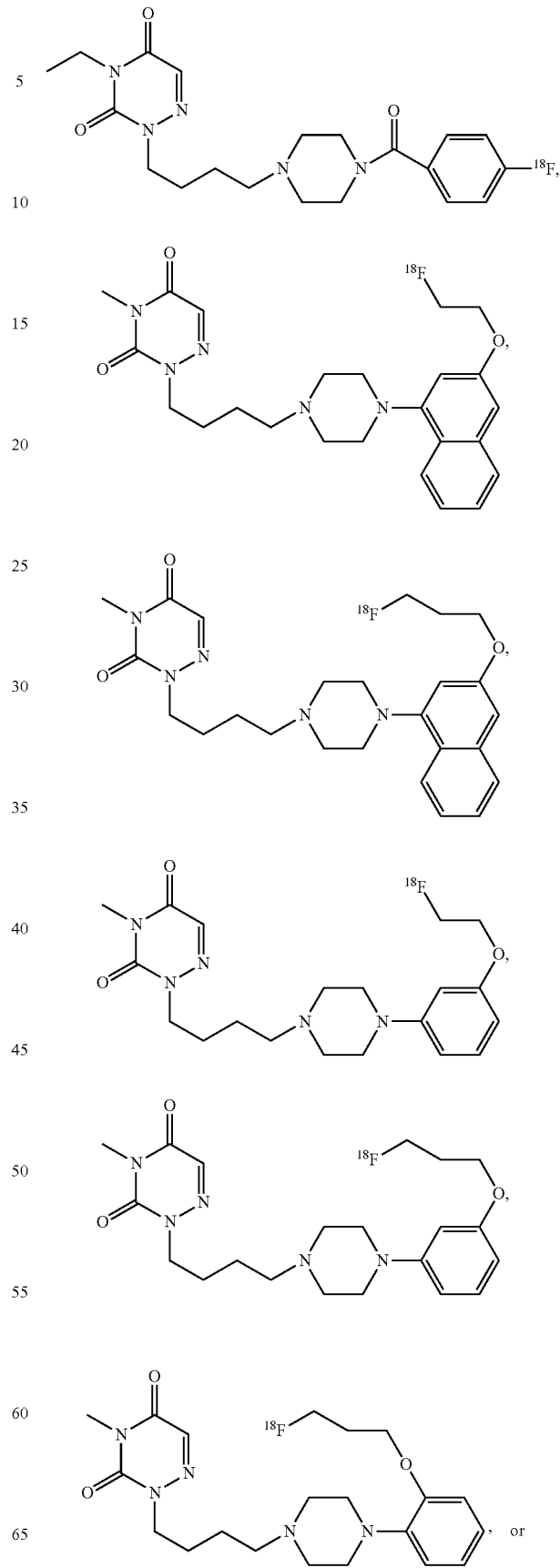

-continued

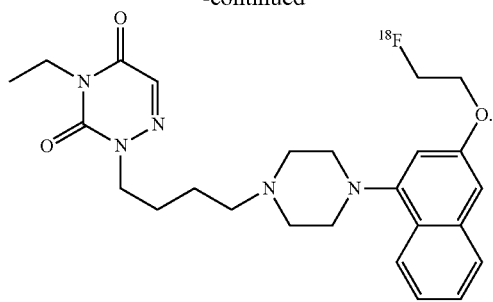

In still another embodiment, Radiolabeled Compounds of Formula (Ic) include:

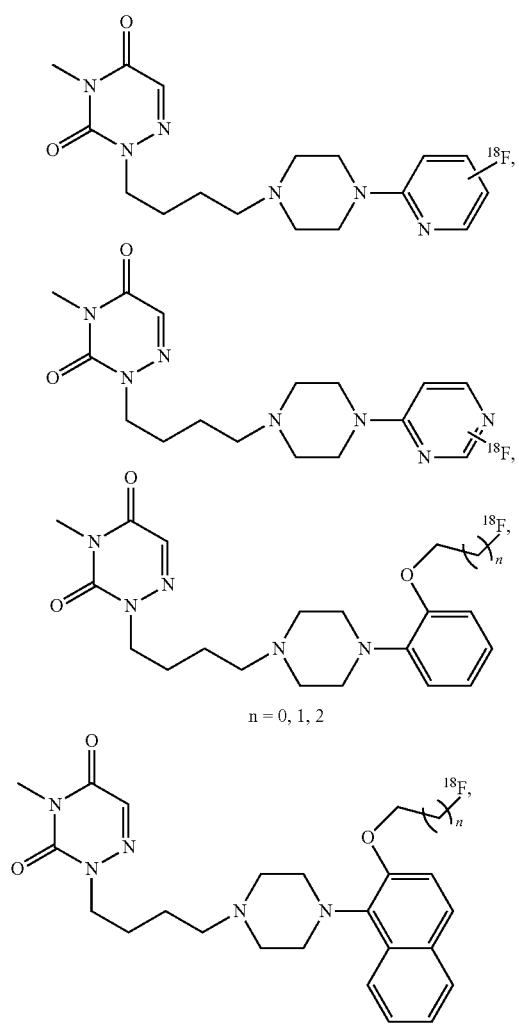

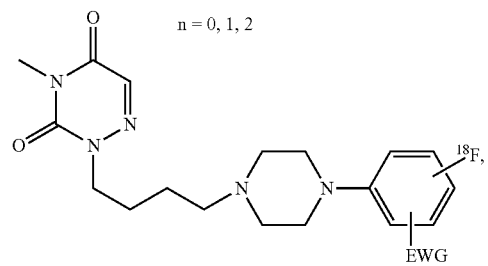

where EWG is a electron-withdrawing group, such as halogens (e.g., F, Cl, Br), amides, nitriles (e.g., CN), carbonyls (e.g., $C(O)R^5$), nitro groups (e.g., $NO_2$), sulfonic acid (e.g., $S(O_2)OH$), sulfone (e.g., $S(O_2)R$), haloalkyl (e.g., $CF_3$), and the like.

In still other embodiments, the Radiolabeled Compounds of Formula (Ic) include:

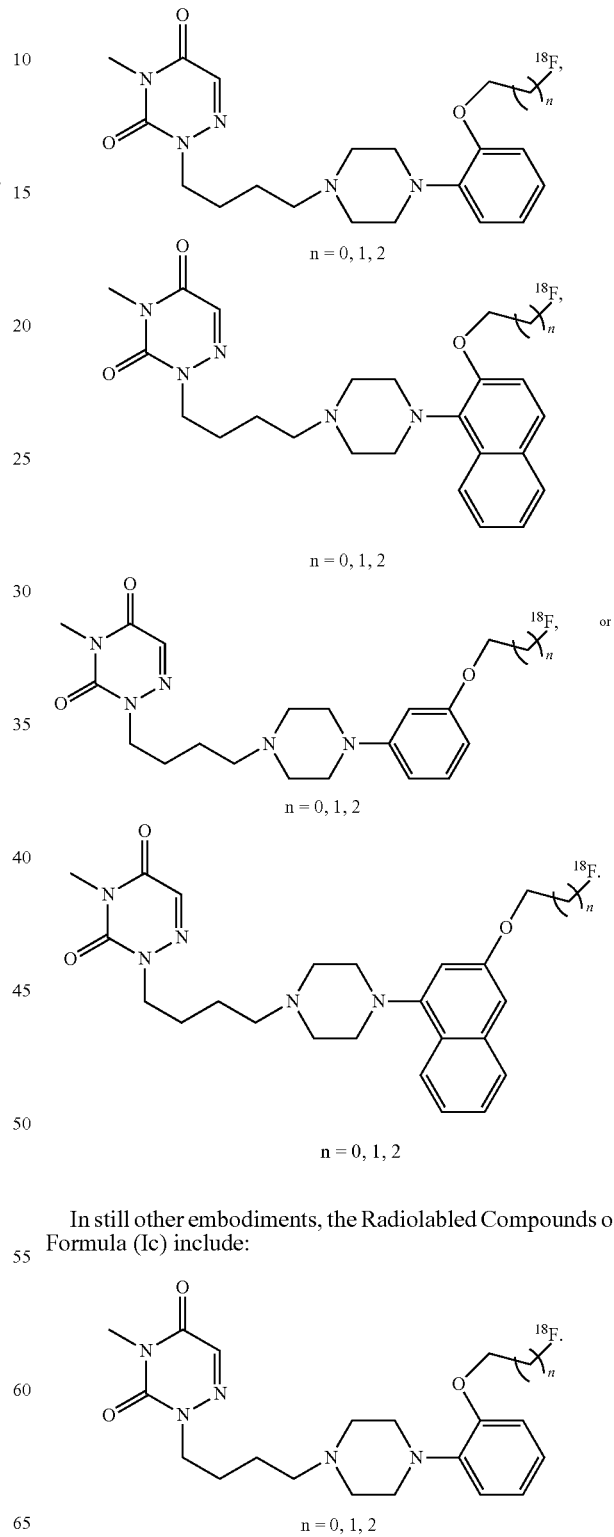

In still other embodiments, the Radiolabeled Compounds of Formula (Ic) include:

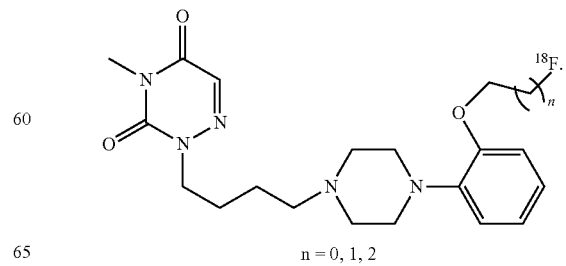

In yet another embodiment, the Radiolabled Compounds of Formula (Ic) include:

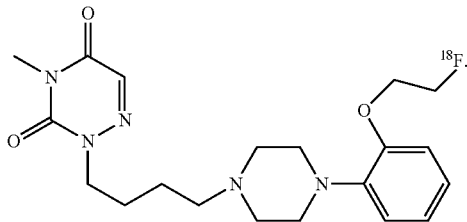

The Radiolabeled Compounds of Formula (I) can act as agonists or antagonists of the 5-$HT_{1A}$ receptor.

In one embodiment, a Radiolabeled Compound of Formula (I) is an antagonist of the 5-$HT_{1A}$ receptor.

In another embodiment, a Radiolabeled Compound of Formula (I) is an agonist of the 5-$HT_{1A}$ receptor.

The Radiolabeled Compounds of Formula (II)

As stated above, the present invention encompasses Radiolabeled Compounds having the Formula (II):

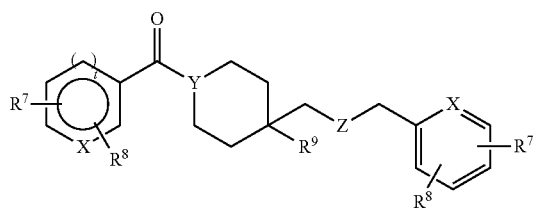

or pharmaceutically acceptable salts thereof, wherein X, Y, Z, $R^7$, $R^8$, $R^9$ and t are as defined above for the Radiolabeled Compounds of Formula (II).

In one embodiment, each $R^7$ is independently —H, —F, —Cl, a straight or branched chain saturated aliphatic hydrocarbon radical containing 1 to 5 carbon atoms such as methyl, ethyl, propyl, butyl, pentyl, isopropyl, 1-methyl-ethyl, 1-methyl-propyl, 1-methyl-butyl, 2-methyl-propyl, 2-methyl-butyl, 3-methyl-butyl, 1-ethyl-propyl, or 2-ethyl-propyl; a fluoroalkyl radical such as fluoromethyl, difluoromethyl, trifluoromethyl, —CH(F)$CH_3$ or —$CF_2CH_3$; a cyclopropyl, cyclobutyl, or cyclopentyl radical; a substituted or unsubstituted 5-membered aromatic heterocyclic group containing 1 to 3 heteroatoms selected from nitrogen, oxygen, and sulfur, such that the heterocycle cannot have more than one sulfur ring atom or more than one oxygen ring atom; —$OR^{10}$ or —$SR^{10}$ where $R^{10}$ is independently a straight or branched chain saturated aliphatic hydrocarbon radical containing 1 to 5 carbon atoms, a monofluoromethyl or trifluoromethyl radical, a cyclopropyl radical, a cyclobutyl radical, or a cyclopentyl radical; or an alkoxycarbonyl group such as —OC(O)$CH_3$ or —OC(O)—$CH_2CH_3$.

In another embodiment, each $R^8$ is independently —$Z^a$—$R^{12}$, —H, —F, —Cl, a straight or branched chain saturated aliphatic hydrocarbon radical containing 1 to 5 carbon atoms such as methyl, ethyl, propyl, butyl, pentyl, isopropyl, 1-methyl-ethyl, 1-methyl-propyl, 1-methyl-butyl, 2-methyl-propyl, 2-methyl-butyl, 3-methyl-butyl, 1-ethyl-propyl, or 2-ethyl-propyl; a fluoroalkyl radical such as fluoromethyl, difluoromethyl, trifluoromethyl, —CH(F)$CH_3$ or —$CF_2CH_3$; a cyclopropyl, cyclobutyl, or cyclopentyl radical; a substituted or unsubstituted 5-membered aromatic heterocyclic group containing 1 to 3 heteroatoms selected from nitrogen, oxygen, and sulfur, such that the heterocycle cannot have more than one sulfur ring atom or more than one oxygen ring atom; —$OR^{10}$ or —$SR^{10}$ where $R^{10}$ is independently a straight or branched chain saturated aliphatic hydrocarbon radical containing 1 to 5 carbon atoms, a monofluoromethyl or trifluoromethyl radical, a cyclopropyl radical, a cyclobutyl radical, or a cyclopentyl radical; or an alkoxycarbonyl group such as OC(O)$CH_3$ or —OC(O)—$CH_2CH_3$.

In still another embodiment, $R^{12}$ is —$^{11}$C-labeled $C_1$-$C_6$ alkyl, —$^{11}$C-labeled $C_2$-$C_6$ alkenyl, —$^{11}$C-labeled $C_2$-$C_6$ alkynyl, —($^{11}$C-labeled $C_1$-$C_6$ alkylene)-aryl, —($^{11}$C-labeled $C_2$-$C_6$ alkenylene)-aryl, or —($^{11}$C-labeled $C_2$-$C_6$ alkynylene)-aryl.

In a further embodiment, $Z^a$ is —O—, —S—, or —NH—.
In another embodiment, $R^9$ is —H or —F.
In still another embodiment X is —N—.
In yet another embodiment Y is —N—.
In a further embodiment Z is —NH—.
In another embodiment t is 1.

The Radiolabeled Compounds of Formula (II) can act as agonists or antagonists of the 5-$HT_{1A}$ receptor.

In one embodiment, a Radiolabeled Compound of Formula (II) is an antagonist of the 5-$HT_{1A}$ receptor.

In another embodiment, a Radiolabeled Compound of Formula (II) is an agonist of the 5-$HT_{1A}$ receptor.

Methods for Making the Radiolabeled Compounds of Formula (I)

The Radiolabeled Compounds of Formula (I) can be made, for example, using the synthetic procedures outlined below in Schemes 1-3.

Scheme 1 shows exemplary methods for making the Radiolabeled Compounds of Formula (I).

Scheme 1

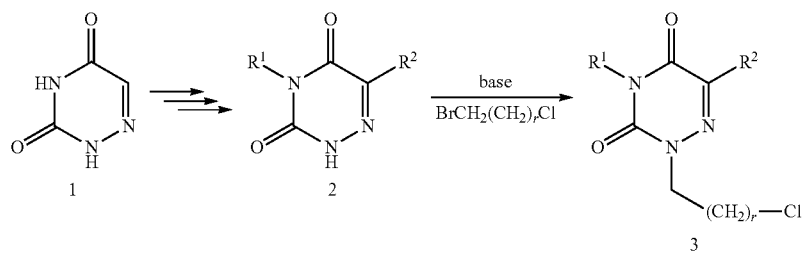

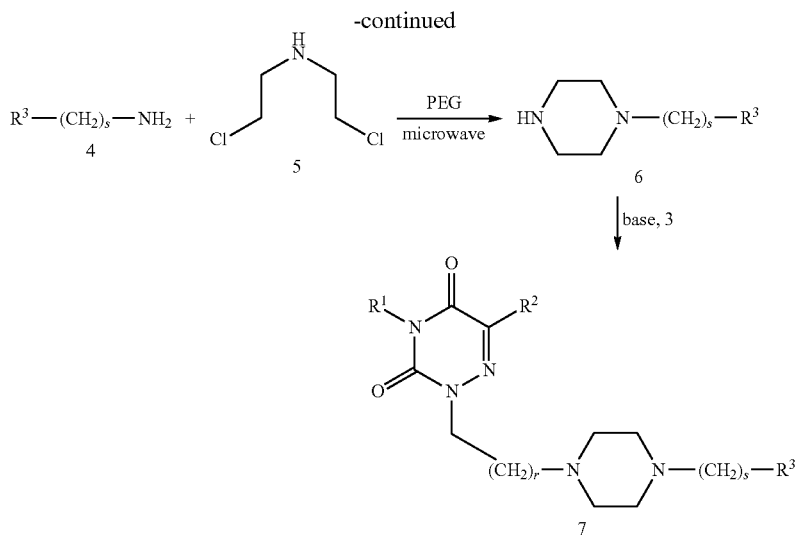

wherein r, s, $R^1$, $R^2$ and $R^3$ are defined above for the Compounds of Formula (I).

The heterocyclic compound 1 can be used as is or can be derivatized using methods well-known to one of ordinary skill in the art of organic synthesis to prepare compounds of formula 2 wherein one or both of $R^1$ and $R^2$ are other than hydrogen. The compounds of Formula 2 are then alkylated using an alkylating agent, for example $BrCH_2(CH_2)_rCl$, in the presence of a base to provide the synthetic intermediates of Formula 3.

An amine of Formula 4 can be reacted with an amine such as di-(2-chloroethyl)amine using microwave irradiation to provide the piperazine intermediates of formula 6. Finally, a compound of Formula 6 is coupled with a compound of Formula 3 in the presence of a base to provide the Compounds of Formula 7.

It will be apparent to one of ordinary skill in the art that radiolabeled group $R^6$, which is a substituent on group $R^3$ in the compounds of Formula (I) may be present in the compounds of Formula 4 or alternatively may be absent from the compounds of Formula 4. In the latter case, the radiolabeled group $R^6$ may be attached to group $R^3$ in any step of the synthesis, or alternatively, may be attached to an intact compound of Formula 7.

Scheme 2 shows exemplary methods for attaching the following radiolabeled groups to the $R^3$ group of a precursor to a Radiolabeled Compound of Formula (I): $^{11}$C-labeled $C_1$-$C_6$ alkyl, $^{11}$C-labeled $C_2$-$C_6$ alkenyl, $^{11}$C-labeled $C_2$-$C_6$ alkynyl, ($^{11}$C-labeled $C_1$-$C_6$ alkylene)-aryl, ($^{11}$C-labeled $C_2$-$C_6$ alkenylene)-aryl, ($^{11}$C-labeled $C_2$-$C_6$ alkynylene)-aryl, $^{18}$F-labeled $C_1$-$C_6$ alkyl, $^{18}$F-labeled $C_2$-$C_6$ alkenyl, $^{18}$F-labeled $C_2$-$C_6$ alkynyl, ($^{18}$F-labeled $C_1$-$C_6$ alkylene)-aryl, ($^{18}$F-labeled $C_2$-$C_6$ alkenylene)-aryl, or ($^{18}$F-labeled $C_2$-$C_6$ alkynylene)-aryl.

Scheme 2

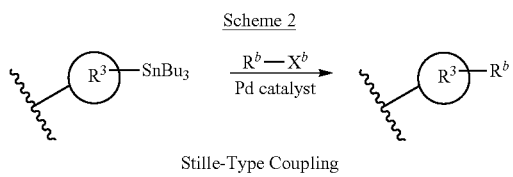

Stille-Type Coupling

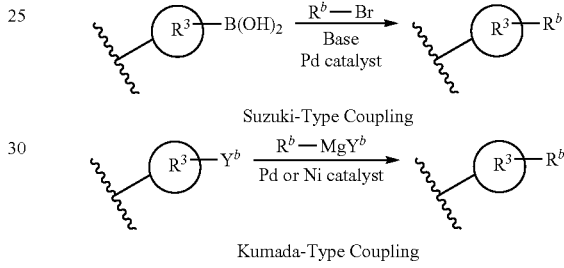

Suzuki-Type Coupling

Kumada-Type Coupling wherein $R^3$ is defined above for the Radiolabeled Compounds of Formula (I); $X^b$ is Cl, Br, I, or OTf; $R^b$ is $^{11}$C-labeled $C_1$-$C_6$ alkyl, $^{11}$C-labeled $C_2$-$C_6$ alkenyl, $^{11}$C-labeled $C_2$-$C_6$ alkynyl, ($^{11}$C-labeled $C_1$-$C_6$ alkylene)-aryl, ($^{11}$C-labeled $C_2$-$C_6$ alkenylene)-aryl, ($^{11}$C-labeled $C_2$-$C_6$ alkynylene)-aryl, $^{18}$F-labeled $C_1$-$C_6$ alkyl, $^{18}$F-labeled $C_2$-$C_6$ alkenyl, $^{18}$F-labeled $C_2$-$C_6$ alkynyl, ($^{18}$F-labeled $C_1$-$C_6$ alkylene)-aryl, ($^{18}$F-labeled $C_2$-$C_6$ alkenylene)-aryl, or ($^{18}$F-labeled $C_2$-$C_6$ alkynylene)-aryl; and each occurrence of $Y^b$ is independently Cl, Br, or I.

An $R^3$ group of a precursor to a Radiolabeled piperazine Compound of formula (I) can be substituted with a radiolabeled group at any point during the synthetic route outlined in Scheme 1. As outlined in Scheme 2, the unlabeled $R^3$ group of a Compound of formula 4, 6 or 7 as shown in Scheme 1 can be subjected to a cross coupling, such as palladium- or nickel-catalyzed coupling process including, but not limited to a Suzuki coupling (A. Suzuki, *Pure Appl. Chem.* 1991, 63:419-422; G. A. Molander, *Curr. Opin. Drug Discov. Devel.* 2009, 12(6):811-23), a Kumada coupling (M. Kumada, *Pure Appl. Chem.* 1980, 52:669), or a Stille coupling (J. K. Stille, *Angew. Chem. Int. Ed.* 1986, 25:508-524) process to provide a product which contains an $R^3$ group that is substituted with any of the following radiolabeled groups: —$^{11}$C-labeled $C_1$-$C_6$ alkyl, —$^{11}$C-labeled $C_2$-$C_6$ alkenyl, —$^{11}$C-labeled $C_2$-$C_6$ alkynyl, —($^{11}$C-labeled $C_1$-$C_6$ alkylene)-aryl, —($^{11}$C-labeled $C_2$-$C_6$ alkenylene)-aryl, —($^{11}$C-labeled $C_2$-$C_6$ alkynylene)-aryl, —$^{18}$F-labeled $C_1$-$C_6$ alkyl, —$^{18}$F-labeled $C_2$-$C_6$ alkenyl, —$^{18}$F-labeled $C_2$-$C_6$ alkynyl, —($^{18}$F-labeled $C_1$-$C_6$ alkylene)-aryl, —($^{18}$F-labeled $C_2$-$C_6$ alkenylene)-aryl, or —($^{18}$F-labeled $C_2$-$C_6$ alkynylene)-aryl.

Scheme 3 shows methods for attaching radiolabeled groups of formula $Z^c$—$R^c$ to an $R^3$ group of a precursor to a Radiolabeled Compound of Formula (I), wherein $Z^c$ is O, S, or NH; and $R^c$ is $^{11}$C-labeled $C_1$-$C_6$ alkyl, $^{11}$C-labeled $C_2$-$C_6$ alkenyl, $^{11}$C-labeled $C_2$-$C_6$ alkynyl, ($^{11}$C-labeled $C_1$-$C_6$ alkylene)-aryl, ($^{11}$C-labeled $C_2$-$C_6$ alkenylene)-aryl, ($^{11}$C-labeled $C_2$-$C_6$ alkynylene)-aryl, $^{18}$F-labeled $C_1$-$C_6$ alkyl, $^{18}$F-labeled $C_2$-$C_6$ alkenyl, $^{18}$F-labeled $C_2$-$C_6$ alkynyl, ($^{18}$F-labeled $C_1$-$C_6$ alkylene)-aryl, ($^{18}$F-labeled $C_2$-$C_6$ alkenylene)-aryl, or ($^{18}$F-labeled $C_2$-$C_6$ alkynylene)-aryl.

Scheme 3

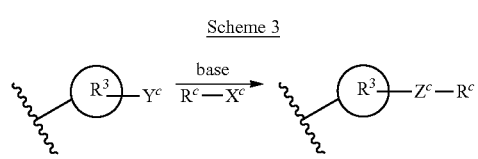

wherein $R^3$ is defined above for the Radiolabeled Compounds of Formula (I); $R^c$ is $^{11}$C-labeled $C_1$-$C_6$ alkyl, $^{11}$C-labeled $C_2$-$C_6$ alkenyl, $^{11}$C-labeled $C_2$-$C_6$ alkynyl, ($^{11}$C-labeled $C_1$-$C_6$ alkylene)-aryl, ($^{11}$C-labeled $C_2$-$C_6$ alkenylene)-aryl, ($^{11}$C-labeled $C_2$-$C_6$ alkynylene)-aryl), $^{18}$F-labeled $C_1$-$C_6$ alkyl, $^{18}$F-labeled $C_2$-$C_6$ alkenyl, $^{18}$F-labeled $C_2$-$C_6$ alkynyl, ($^{18}$F-labeled $C_1$-$C_6$ alkylene)-aryl, ($^{18}$F-labeled $C_2$-$C_6$ alkenylene)-aryl, or ($^{18}$F-labeled $C_2$-$C_6$ alkynylene)-aryl; $X^c$ is a leaving group such as, for example, Cl, Br, I, OMs, OTs, or OTf; $Y^c$ is OH, SH, or NH$_2$; and $Z^c$ is O, S, or NH.

An OH, NH$_2$, or SH group attached to an $R^3$ group of a compound of Formula 4, 6 or 7 as shown in Scheme 1 can be treated with base and the resulting oxygen, sulfur, or nitrogen anion can be reacted with a group having the formula $R^c$—$X^c$, wherein $X^c$ is a leaving group such as, for example, Cl, Br, I, OMs, OTs, or OTf, to provide a product which contains an $R^3$ group that is substituted with a radiolabeled group of formula $Z^c$—$R^c$, wherein $Z^c$ is O, S, or NH; and $R^c$ is $^{11}$C-labeled $C_1$-$C_6$ alkyl, $^{11}$C-labeled $C_2$-$C_6$ alkenyl, $^{11}$C-labeled $C_2$-$C_6$ alkynyl, ($^{11}$C-labeled $C_1$-$C_6$ alkylene)-aryl, ($^{11}$C-labeled $C_2$-$C_6$ alkenylene)-aryl, ($^{11}$C-labeled $C_2$-$C_6$ alkynylene)-aryl, $^{18}$F-labeled $C_1$-$C_6$ alkyl, $^{18}$F-labeled $C_2$-$C_6$ alkenyl, $^{18}$F-labeled $C_2$-$C_6$ alkynyl, ($^{18}$F-labeled $C_1$-$C_6$ alkylene)-aryl, ($^{18}$F-labeled $C_2$-$C_6$ alkenylene)-aryl, or ($^{18}$F-labeled $C_2$-$C_6$ alkynylene)-aryl. $R^c$ groups containing a radiolabel such as $^{18}$F are installed from a precursor containing a leaving group such as, for example, -OTs, -OMs, or -OTs. In one exemplary method, an $R^c$ group comprised of a tosylate (-OTs) is reacted with K$^{18}$F and Kryptofix in the presence of a base (*J. Nuc. Med.* 2003, 44, 1700-1706) to provide the radiolabeled compounds. Still other methods for synthesizing the Radiolabeled Compounds will be apparent to those of skill in the art.

Specifically, the following scheme (Scheme 4) shows exemplary methods for attaching bromine, iodine, and tritium radioisotopes to, for example, an $R^3$ group of the compound Formula (I). Each of the starting substituents shown below represents the entire or a portion of the $R^3$ group of the compound of Formula (I), where Br can be $^{75}$Br or $^{76}$Br and I can be $^{120}$I, $^{123}$I, $^{124}$I, $^{125}$I, or $^{131}$I.

Scheme 4

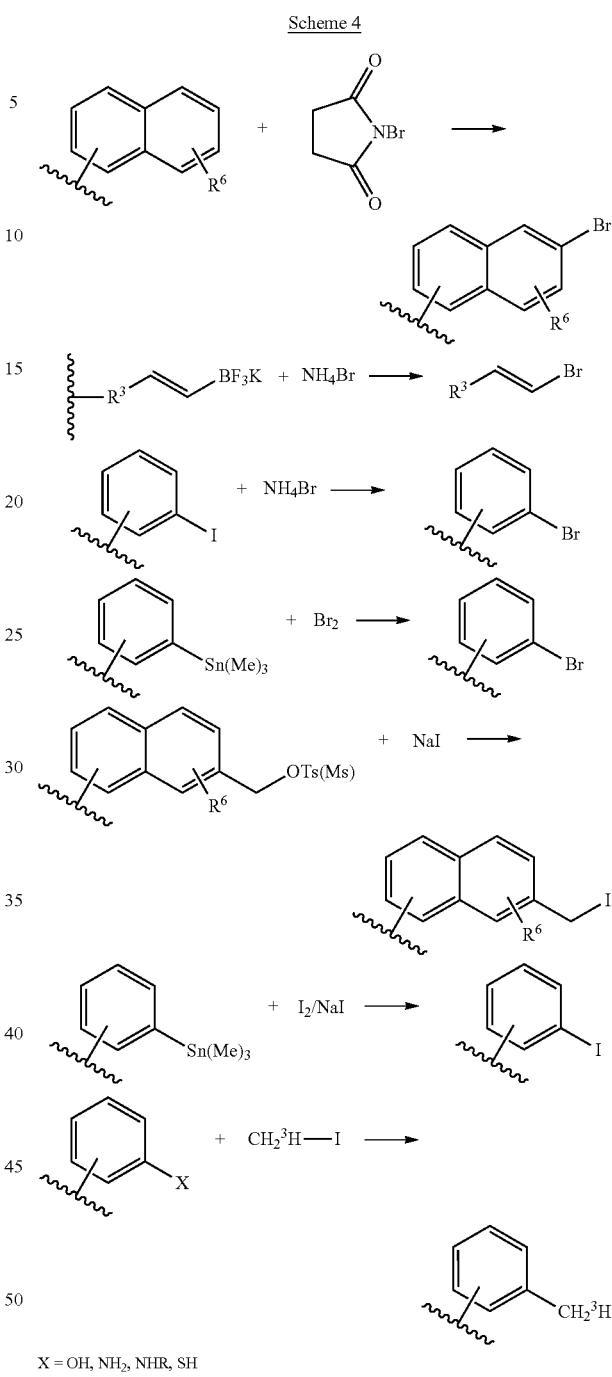

X = OH, NH$_2$, NHR, SH

Radiolabeled compounds of Formula (I) that can be made using the methods of the invention include, for example, the compounds having the Formula (A), (B), (C), (D), (E), (F) and pharmaceutically acceptable salts thereof.

Methods for Making the Radiolabeled Compounds of Formula (II)

The Radiolabeled Compounds of Formula (II) can be made, for example, using the synthetic procedures outlined in Scheme 5 below.

Scheme 5

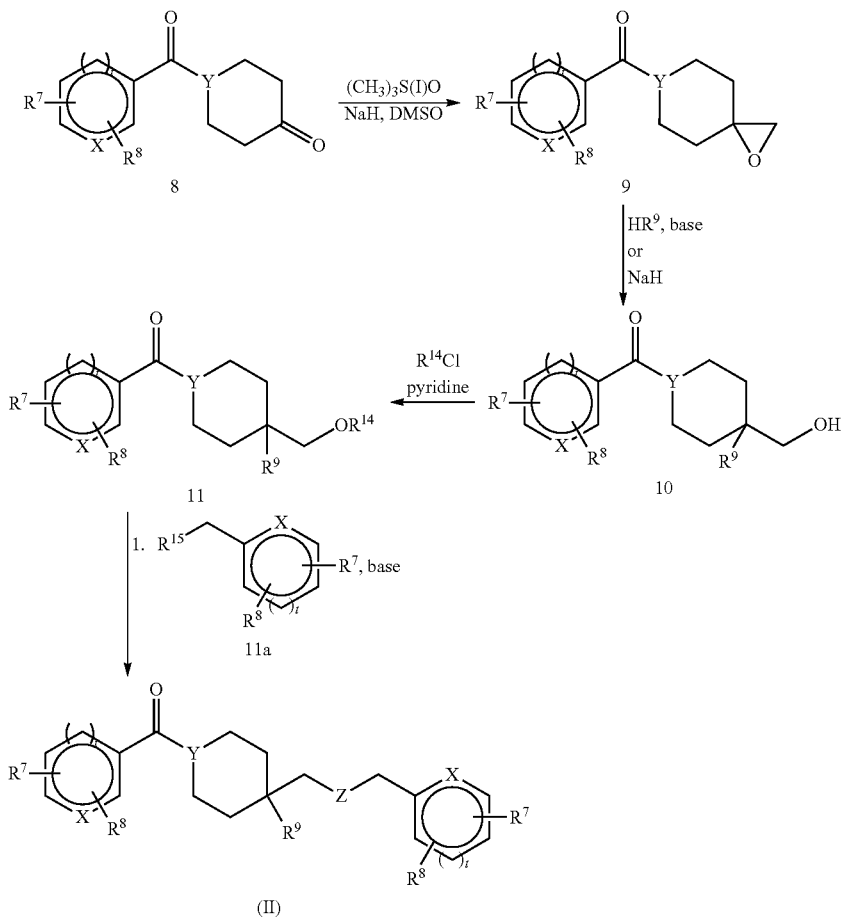

wherein $R^7$, $R^8$, $R^9$, X, Y, Z, and t are defined above for the Radiolabeled Compounds of Formula (II); $R^{13}$ is —F or —NO$_2$; $R^{14}$ is a leaving group such as -mesyl, -tosyl or -triflyl; and $R^{15}$ is —OH, —SH, or —NH$_2$.

A compound of Formula 8 can be reacted with trimethylsulfoxonium iodide in the presence of NaH to provide an epoxide compound of formula 9. The epoxide ring of Formula 9 can then be reacted with: (1) a compound of formula HR$^9$ in the presence of base, where $R^9$ is -halo to provide a compound of Formula 10 wherein $R^9$ is -halo; or (2) NaH to provide a compound of Formula 10 wherein $R^9$ is —H. The hydroxyl group of a compound of Formula 10 can be converted to a leaving group by reacting with a compound of formula R$^{14}$Cl in the presence of a non-nucleophilic base, such as pyridine to provide a compound of Formula 11. Finally, a compound of Formula 11 can be coupled with a compound of Formula 11a in the presence of base and the resultant adduct can then be reacted with Kryptofix 222/[$^{18}$F] and potassium carbonate as described in de Vries et al., *Journal of Nuclear Medicine* 2003, 44:1700-1706, to provide the Radiolabeled Compounds of Formula (II).

Advantages

In some embodiments, the bromine and iodine Radiolabeled Compounds of the present invention provide longer half-life, which provide significant advantages over compounds labeled with $^{11}$C or $^{18}$F. In many compounds, $^{11}$C has a half-life of about 20 minutes and $^{18}$F has a half life of about 110 minutes. Often, such short half-lives require either on-site synthesis of the radiolabeled compound or drastically limit the geographical location where the Radiolabeled Compounds can be utilized relative to the synthesis center.

In some embodiments, the radioisotopes utilized in the Radiolabeled Compounds of the present invention provide comparable and longer half-lives. For example, $^{75}$Br has a half life of 96.7 minutes, $^{76}$Br has a half-life of 16.2 hours, $^{120}$I has a half life of 81.6 minutes, $^{123}$I has a half life of 13.22 hours, $^{124}$I has a half life of 4.17 days, $^{125}$I 59.4 days, $^{131}$I has a half life of 8.02 days, and $^3$H has a half life of 12.32 years.

In some embodiments, the Radiolabeled Compounds of the present invention are highly selective for 5-HT$_{1A}$, enable imaging in vivo, and/or provide a more meaningful functional assessment of the receptor. Thus, in some embodiments, the Radiolabeled Compounds of the present invention exhibit improved selectivity over other receptors such as, for example, $\alpha_{1a}$, 5-HT$_7$, dopamine receptors, and sigma receptors such as σ1.

Introducing such new radioisotopes brings a host of new challenges. For example, the labeling sites where the radioisotopes can be attached may be different. Taking iodine as an example, iodine is larger and has a different charge state compared to carbon or fluorine. Taking tritium as the other example, tritium is much smaller and also has a different charge state compared to carbon or fluorine.

Uses of the Radiolabeled Compounds as Radiological Imaging Agents

The Radiolabeled Compounds can be used as imaging agents to image one or more 5-HT$_{1A}$ receptors in a subject.

In one embodiment, the present invention relates to the use of a Radiolabeled Compound for detecting one or more 5-HT$_{1A}$ receptors in vivo. In one embodiment, the detecting step employs a nuclear imaging technique selected from the group consisting of positron emission tomography (PET) and single photon emission computed tomography (SPECT) for monitoring a distribution of the imaging agent within the subject or a portion thereof. In particular, the present methods for detecting 5-HT$_{1A}$ receptors in vivo contemplate the use of PET, where the imaging probe is a Radiolabeled Compound.

In another embodiment, the invention provides a method for imaging one or more 5-HT$_{1A}$ receptors in a subject comprising the steps: (a) administering to the subject an imaging-effective amount of a Radiolabeled Compound or pharmaceutically acceptable salt thereof, and (b) detecting the radioactive emission of the compound or salt thereof administered in step (a).

In one embodiment, the detecting step is carried out using PET. In another embodiment, the detecting step is carried out using SPECT.

In another embodiment, the 5-HT$_{1A}$ receptors being imaged are in the brain of the subject.

Methods for imaging, and thereby detecting, 5-HT$_{1A}$ receptors in vivo are desirable in order to screen individuals for psychiatric neurological disorders or for diseases, disorders, states or conditions, or predispositions to neurological disorders, diseases, states or conditions, that are related to the binding of serotonin to 5-HT$_{1A}$ receptors. For example, the following list of processes, diseases or disorders may involve alterations in normal binding of serotonin to 5-HT$_{1A}$ receptors: mood disorders, such as a major depressive disorder or bipolar disorder; an eating disorder, such as anorexia nervosa or bulimia nervosa; an addictive disorder, such as drug addiction, alcoholism, or sexual addiction; a sleep disorder, such as insomnia, narcolepsy or catalepsy; a disease associated with cognitive dysfunction, such as Parkinson's disease, or schizophrenia; a neurodegenerative disease, such as stroke, Alzheimer's disease, Parkinson's disease, amyotrophic lateral sclerosis (ALS), or temporal lobe epilepsy; a pain disorder, including neuropathic pain or cancer pain; psychotic disorders such as schizophrenia; a movement disorder, such as Parkinson's disease; an anxiety disorder such as panic disorder, post-traumatic stress disorder, social anxiety disorder, schizophrenia, or obsessive-compulsive disorder or social phobia; a seizure disorder, such as temporal lobe epilepsy.

Further, Radiolabeled Compounds which are selective for the 5-HT$_{1A}$ receptor can be used to screen for individuals who are more likely to respond to drugs that act on these receptors or susceptible to side effects of drugs which bind to the 5-HT$_{1A}$ receptor, as manifested by an increased detection of radiolabeled 5-HT$_{1A}$ selective agents in specified tissue compartments. These compounds can used to identify the dose range of drugs to treat illnesses and disorders that work by binding to this receptor. Thus, in some embodiments, the methods comprise screening for individuals who are more likely to respond to drugs that act on 5-HT$_{1A}$ or are susceptible to side effects from drugs that bind to the 5-HT$_{1A}$ receptor.

The Radiolabeled Compounds and compositions may be useful in the identification, prophylaxis and/or treatment of afflictions related to the function of the 5-HT receptor. In one embodiment, the compounds and/or compositions are useful in diagnosing afflictions related to the function of the 5-HT receptor. In another embodiment, the compounds and/or compositions are useful in diagnosing predisposition to afflictions related to the function of the 5-HT receptor.

In one embodiment, the Radiolabeled Compounds have high specific activity. In one embodiment, the invention provides Radiolabeled Compounds having a specific activity that is greater than about 1,000 Ci/micromole. In certain embodiments, the specific activity is from about 500 to about 1,000 Ci/mmol; about 1,000 to about 2,000 Ci/mmol; about 2,000 to about 3,000 Ci/mmol; about 3,000 to about 4,000 Ci/mmol; about 4,000 to about 5,000 Ci/mmol; or greater than 5,000 Ci/mmol; wherein any of the aforementioned ranges may be combined and/or overlap, and wherein the lower and/or upper limits of any of the aforementioned ranges may combined as appropriate.

Further, the Radiolabeled Compounds may have a high affinity and specificity to the 5-HT$_{1A}$ receptor. In one embodiment, the Radiolabeled Compounds have a 5-HT$_{1A}$ receptor binding affinity that is from about 2-times to about 100,000-times greater than the binding affinity for any of the other known transporters, receptors, enzymes, and peptides. In certain embodiments, the binding affinity that is from about 2-times to about 5-times greater; about 5-times to about 10-times greater; about 10-times to about 20-times greater; about 20-times to about 50-times greater; about 50-times to about 100-times greater; about 100-times to about 200-times greater; about 200-times to about 300-times greater; about 300-times to about 400-times greater; about 400-times to about 500-times greater; about 500-times to about 1,000-times greater; about 1,000-times to about 2,000-times greater; about 2,000-times to about 3,000-times greater; about 3,000-times to about 4,000-times greater; about 4,000-times to about 5,000-times greater; about 5,000-times to about 10,000-times greater; about 10,000-times to about 50,000-times greater; or about 50,000-times to about 100,000-times greater; wherein any of the aforementioned ranges may be combined and/or overlap, and wherein the lower and/or upper limits of any of the aforementioned ranges may combined as appropriate.

In some embodiments, the Radiolabeled Compounds have a 5-HT$_{1A}$ receptor binding affinity that is greater than the binding affinity for receptors such as, for example, $\alpha_{1a}$, 5-HT$_7$, D$_2$, D$_3$, D$_4$, and $\sigma_1$. In certain embodiments, the binding affinity of the Radiolabeled Compounds for receptors other than 5-HT$_{1A}$ is from about 5 nM to about 10,000 nM; about 5 nM to about 10 nM; about 5 nM to about 20 nM; about 20 nM to about 50 nM; about 50 nM to about 100 nM; about 100 nM to about 500 nM; about 500 nM to about 1 µM; about 1 µM to about 2 µM; about 2 µM to about 3 µM; about 3 µM to about 5 µM; about 5 µM to about 10 µM; or greater than about 10 µM; wherein any of the aforementioned ranges may be combined and/or overlap, and wherein the lower and/or upper limits of any of the aforementioned ranges may combined as appropriate for any receptor other than 5-HT$_{1A}$.

The Radiolabeled Compounds can be used to detect and/or quantitatively measure 5-HT$_{1A}$ receptor levels in subjects, including humans. The Radiolabeled Compounds can also be used to measure and/or detect 5-HT$_{1A}$ receptors in 5-HT$_{1A}$ receptor related diseases, conditions and disorders, including but not limited to, mood disorders, such as a major depressive disorder or bipolar disorder; an eating disorder, such as anorexia nervosa or bulimia nervosa; an addictive disorder, such as drug addiction, alcoholism, or sexual addiction; a sleep disorder, such as insomnia, narcolepsy or catalepsy; a disease associated with cognitive dysfunction, such as Parkinson's disease, or schizophrenia; a neurodegenerative disease, such as stroke, Alzheimer's disease, Parkinson's disease, amyotrophic lateral sclerosis (ALS), or temporal lobe epilepsy; a pain disorder, including neuropathic pain or cancer pain; psychotic disorders such as schizophrenia; a movement disorder, such as Parkinson's disease; an anxiety disorder such as panic disorder, post-traumatic stress disorder, social anxiety disorder, schizophrenia, or obsessive-compulsive disorder or social phobia; a seizure disorder, such as temporal lobe epilepsy.

The ability to quantitatively measure $5\text{-HT}_{1A}$ receptor levels in a subject is useful for pre-screening subjects and in one embodiment, a Radiolabeled Compound can be administered to a subject to help determine whether the subject is likely to be a responder or non-responder to medicinal agents which bind to $5\text{-HT}_{1A}$ receptors. The ability to quantitatively measure $5\text{-HT}_{1A}$ receptor levels in a subject is useful for pre-screening clinical trial patient populations. In one embodiment, the methods comprise pre-screening patient populations to measure $5\text{-HT}_{1A}$ receptor levels in subjects.

The Radiolabeled Compounds can also be used to detect or monitor processes, diseases or disorders that may involve the binding of serotonin to $5\text{-HT}_{1A}$ receptors, including but not limited to, mood disorders, such as a major depressive disorder or bipolar disorder; an eating disorder, such as anorexia nervosa or bulimia nervosa; an addictive disorder, such as drug addiction, alcoholism, or sexual addiction; a sleep disorder, such as insomnia, narcolepsy or catalepsy; a disease associated with cognitive dysfunction, such as Parkinson's disease, or schizophrenia; a neurodegenerative disease, such as stroke, Alzheimer's disease, Parkinson's disease, amyotrophic lateral sclerosis (ALS), or temporal lobe epilepsy; a pain disorder, including neuropathic pain or cancer pain; psychotic disorders such as schizophrenia; a movement disorder, such as Parkinson's disease; an anxiety disorder such as panic disorder, post-traumatic stress disorder, social anxiety disorder, schizophrenia, or obsessive-compulsive disorder or social phobia; a seizure disorder, such as temporal lobe epilepsy.

The Radiolabeled can also be used to help determine the capacity that one or more $5\text{-HT}_{1A}$ receptors have for signaling. In this embodiment, the present methods for imaging $5\text{-HT}_{1A}$ receptors can be used to determine the percentage of $5\text{-HT}_{1A}$ receptors that are at a high affinity state. In a specific embodiment, the Radiolabeled Compound being administered for imaging one or more $5\text{-HT}_{1A}$ receptors is an agonist of the $5\text{-HT}_{1A}$ receptor.

Further, the Radiolabeled Compounds can be used to screen for individuals who are more susceptible to side effects of agents which bind to $5\text{-HT}_{1A}$ receptors, as manifested by an increased detection of the Radiolabeled Compounds in specified tissue compartments.

Additionally, the Radiolabeled Compounds are useful in drug discovery programs and in one embodiment, can be used to determine the efficacy or receptor occupancy of agents that bind to $5\text{-HT}_{1A}$ receptors when such agents are administered to a subject to treat a disorder whose etiology involves or does not involve the binding of serotonin to one or more $5\text{-HT}_{1A}$ receptors. In another embodiment, the Radiolabeled Compounds can be used to monitor the occupancy rate of $5\text{-HT}_{1A}$ receptors in a subject after the subject has been administered an agent that binds to $5\text{-HT}_{1A}$ receptors. In one embodiment, the occupancy rate of $5\text{-HT}_{1A}$ receptors for experimental drugs can be used to help determine optimal dosage levels of such drugs. In so far as the Radiolabeled Compound is an agonist, it has special advantages in quantifying the receptor occupancy of potential new therapeutic agents that are also agonists and therefore in determining the optimal dose to use for those agents as part of an Investigational New Drug (ND) application process or drug development program and thereby shorten the time period to acquire data for regulatory approval for marketing and general use in treatment. When the Radiolabeled Compound of the present invention is an agonist it will also aid the study and diagnosis of disease by being more sensitive to the quantification of serotonin release and depletion.

Alternatively, the methods for detection can be used to monitor the course of, or treatment thereof, a $5\text{-HT}_{1A}$ receptor related disease in an individual. Thus, whether a particular therapeutic regimen aimed at ameliorating the cause of the disease, or the disease process itself, is effective, can be determined by measuring the decrease of $5\text{-HT}_{1A}$ receptors at suspected sites of disease.

In a further embodiment, the present methods for imaging $5\text{-HT}_{1A}$ receptors can provide images of the location of $5\text{-HT}_{1A}$ receptors and serve as a guide to surgeons who are operating in the area of such receptors. In one embodiment, the surgeon is a neurosurgeon operating on the brain of a subject.

Uses of the Radiolabeled Compounds to Diagnose or Evaluate a Psychiatric Disorder A psychiatric disorder or neurological disorder can be diagnosed or evaluated by administration of an effective amount of a Radiolabeled Compound of the present invention.

Psychiatric disorders that can be diagnosed or evaluated by administering an effective amount of a Radiolabeled Compound of the present invention include, but are not limited to, a mood disorder, such as a major depressive disorder, bipolar disorder, manic depression, depression, cyclothymia, dysthymia, or borderline personality disorder; an eating disorder, such as anorexia nervosa or bulimia; an addictive disorder, such as drug addiction, alcoholism, or sexual addiction; a sleep disorder, such as insomnia or narcolepsy; a disease associated with cognitive dysfunction, such as Alzheimer's disease; a neurodegenerative disease, such as stroke; a pain disorder, including neuropathic pain or cancer pain; psychotic disorders such as schizophrenia; a movement disorder, such as Parkinson's disease; an anxiety disorder such as panic disorder, or obsessive-compulsive disorder or social phobia; a seizure disorder, such as temporal lobe epilepsy.

In one embodiment, the psychiatric disorder is a mood disorder.

In another embodiment, the psychiatric disorder is an eating disorder.

In another embodiment, the psychiatric disorder is an addictive disorder.

In another embodiment, the psychiatric disorder is a disease associated with cognitive dysfunction.

In a specific embodiment, the psychiatric disorder is Alzheimer's disease.

In still another embodiment, the psychiatric disorder is a neurodegenerative disease.

In yet another embodiment, the psychiatric disorder is a pain disorder.

In another embodiment, the psychiatric disorder is a psychotic disorder.

In one embodiment, the psychiatric disorder is a movement disorder.

In another embodiment, the psychiatric disorder is an anxiety disorder.

In still another embodiment, the psychiatric disorder is a seizure disorder.

In yet another embodiment, the psychiatric disorder is an obsessive-compulsive disorder.

Uses of the Radiolabeled Compounds to Stabilize the Mood of a Subject Having a Mood Disorder The mood of a subject having a mood disorder can be stabilized by administration of a therapeutically effective amount of a Radiolabeled Compound of the present invention.

Mood disorders in which the Radiolabeled Compounds of the present invention are useful for stabilizing the mood include, but are not limited to, a major depressive disorder, bipolar disorder, manic depression, depression, cyclothymia, dysthymia, and borderline personality disorder.

In one embodiment, the mood disorder is a major depressive disorder.

In another embodiment, the mood disorder is bipolar disorder.

Examples of conditions treatable or preventable using the Radiolabeled Compounds of the present invention include, but are not limited to, an eating disorder, such as anorexia nervosa or bulimia; drug addiction, alcoholism, or sexual addiction; a sleep disorder, such as insomnia or narcolepsy; a disease associated with cognitive dysfunction, such as Alzheimer's disease; a neurodegenerative disease, such as stroke; a pain disorder, including neuropathic pain or cancer pain; psychotic disorders such as schizophrenia; a movement disorder, such as Parkinson's disease; an anxiety disorder such as panic disorder, or obsessive-compulsive disorder or social phobia; or a seizure disorder, such as temporal lobe epilepsy.

Therapeutic/Diagnostic Administration of the Radiolabeled Compounds

The Radiolabeled Compounds of the present invention are advantageously useful in veterinary and human medicine. As described above, the Radiolabeled Compounds of the present invention are useful for imaging 5-$HT_{1A}$ receptors in a subject.

When administered to a subject, the Radiolabeled Compounds of the present invention can be administered as a component of a composition that comprises a physiologically acceptable carrier or vehicle. The present compositions, which comprise a Radiolabeled Compound of the present invention, can be administered orally or by any other convenient route, for example, by infusion or bolus injection, or by absorption through epithelial or mucocutaneous linings (e.g., oral, rectal, and intestinal mucosa, etc.) and can be administered together with another biologically active agent. Administration can be systemic or local. Various delivery systems are known, e.g., encapsulation in liposomes, microparticles, microcapsules, capsules, etc., and can be administered.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical, particularly to the ears, nose, eyes, or skin. In some instances, administration will result in the release of the Radiolabeled Compounds of the present invention into the bloodstream. The mode of administration is left to the discretion of the practitioner.

In one embodiment, the Radiolabeled Compounds of the present invention are administered orally.

In another embodiment, the Radiolabeled Compounds of the present invention are administered intravenously.

In another embodiment, the Radiolabeled Compounds of the present invention are administered transdermally.

In other embodiments, it can be desirable to administer the Radiolabeled Compounds of the present invention locally. This can be achieved, for example, and not by way of limitation, by local infusion during surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce the Radiolabeled Compounds of the present invention into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler of nebulizer, and formulation with an aerosolizing agent, or via perfusion in a fluorocarbon or a synthetic pulmonary surfactant.

In another embodiment the Radiolabeled Compounds of the present invention can be delivered in a vesicle, in particular a liposome (see Langer, *Science* 249:1527-1533 (1990) and *Liposomes in the Therapy of Infectious Disease and Cancer*, pp. 317-327 and 353-365 (1989)).

In yet another embodiment the Radiolabeled Compounds of the present invention can be delivered in a controlled-release system or sustained-release system (see, e.g., Goodson, in Medical Applications of Controlled Release, supra, vol. 2, pp. 115-138 (1984)). Other controlled or sustained-release systems discussed in the review by Langer, *Science* 249:1527-1533 (1990) can be used. In one embodiment a pump can be used (Langer, *Science* 249:1527-1533 (1990); Sefton, *CRC Crit. Ref. Biomed. Eng.* 14:201 (1987); Buchwald et ah, *Surgery* 88:507 (1980); and Saudek et al., *N. Engl. J Med.* 321:574 (1989)). In another embodiment polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al., *Ann. Neural.* 25:351 (1989); and Howard et al., *J. Neurosurg.* 71:105 (1989)).

The present compositions can optionally comprise a suitable amount of a physiologically acceptable excipient so as to provide the form for proper administration of a Radiolabeled Compound of the present invention to the subject.

Such physiologically acceptable excipients can be liquids, such as water for injection, bacteriostatic water for injection, sterile water for injection, and oils, including those of petroleum, subject, vegetable, or synthetic origin, such as peanut oil, soybean oil, mineral oil, sesame oil and the like. The pharmaceutical excipients can be saline, gum acacia; gelatin, starch paste, talc, keratin, colloidal silica, urea and the like. In addition, auxiliary, stabilizing, thickening, lubricating, and coloring agents can be used. In one embodiment the physiologically acceptable excipients are sterile when administered to a subject. Water is a particularly useful excipient when the Radiolabeled Compound of the present invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills; pellets, capsules, capsules containing liquids, powders, sustained-release formulations, suppositories, emulsions. aerosols, sprays, suspensions, or any other form suitable for use. In one embodiment the composition is in the form of a capsule (see e.g. U.S. Pat. No. 5,698,155). Other examples of suitable physiologically acceptable excipients are described in *Remington's Pharmaceutical Sciences* 1447-1676 (Alfonso R. Gennaro eds., 19th ed. 1995), and subsequent editions, each of which are incorporated herein by reference.

In one embodiment the Radiolabeled Compounds are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment the excipients are of pharmaceutical grade.

In one embodiment, when a Radiolabeled Compound is orally administered, the Radiolabeled Compound is administered in combination with an additional therapeutic agent that can increase the oral bioavailability of the Radiolabeled Compound, as described, for example, in U.S. Pat. No. 6,008, 222. The additional therapeutic agent may be administered separately from the Radiolabeled Compound or the additional agent and the Radiolabeled Compound may be co-administered as part of the same composition. In a specific embodiment, the additional agent that increases the oral bioavailability of a Radiolabeled Compound is nefazodone.

In another embodiment the Radiolabeled Compounds can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Generally, the ingredients are supplied either separately or mixed together in unit dosage form, for example, as a dry lyophilized-powder or water free concentrate in a hermetically sealed container such as an ampule or sachette indicating the quantity of active agent. Where the Radiolabeled Compounds are to be administered by infusion, they can be dispensed, for example, with an infusion bottle containing sterile pharmaceutical grade water or saline. Where the Radiolabeled Compounds are administered by injection, an ampule of sterile water for injection or saline can be provided so that the ingredients can be mixed prior to administration.

Consistent with the pharmaceutical compositions, kits and/or formulations described herein, other additives may be added to reduce radiolysis such as, for example, ascorbic acid. The formulations, kits and/or compositions may further comprise a suitable organic solvent, such as an alcohol, which may be present in amounts up to about 20%. In some embodiments, the alcohol is present from about 1% to about 5%; from about 5% to about 10%; from about 10% to about 15%; or from about 15% to about 20%. In some embodiments, the alcohol is present in about 10%. In some embodiments, the organic solvent is ethanol.

The Radiolabeled Compounds can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598, 123; 4,008,719; 5,674,533; 5,059,595; 5,591,767; 5,120,548; 5,073,543; 5,639,476; 5,431,922; 5,354,556; and 5,733,556, each of which is incorporated herein by reference. Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the Radiolabeled Compounds of the invention. The invention thus encompasses single unit dosage forms suitable for oral administration such as, but not limited to, tablets, capsules, gelcaps, and caplets that are adapted for controlled- or sustained-release. The invention also encompasses transdermal delivery devices, including but not limited to, a transdermal patch and other devices, such as those described in U.S. Pat. No. 5,633,009.

In one embodiment a controlled- or sustained-release composition comprises a minimal amount of a Radiolabeled Compound to image one or more 5-HT$_{1A}$ receptors in a subject. Advantages of controlled- or sustained-release compositions include extended activity of the drug, reduced dosage frequency, and increased subject compliance. In addition, controlled- or sustained-release compositions can favorably affect the time of onset of action or other characteristics, such as blood levels of the Radiolabeled Compound, and can thus reduce the occurrence of adverse side effects.

Controlled- or sustained-release compositions can initially release an amount of a Radiolabeled Compound that promptly produces the desired diagnostic effect, and gradually and continually release other amounts of the Radiolabeled Compound to maintain this level of diagnostic effect over an extended period of time. To maintain a constant level of the Radiolabeled Compound in the body, the Radiolabeled Compound can be released from the dosage form at a rate that will replace the amount of Radiolabeled Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions.

The amount of the Radiolabeled Compound that is effective as an imaging agent to detect one or more 5-HT$_{1A}$ receptors in a subject can be determined using standard clinical and nuclear medicine techniques. In addition, in vitro or in vivo testing can optionally be employed to help identify optimal dosage ranges. The precise dose to be employed will also depend on certain factors—the route of administration, the identity of the subject and the identity of the particular radionuclide being detected- and should be decided according to the judgment of the practitioner and each subject's circumstances in view of, e.g., published clinical studies. Suitable imaging-effective dosage amounts, however, range from about 0.01 mCi to about 30 mCi; about 2 mCi to about 30 mCi; about 10 to about 30 mCi or preferably from about 2 mCi to about 5 mCi. In some embodiments, the Radiolabeled Compounds will have a specific activity of >1000 Ci/micromol at the time of administration to ensure a low injected mass and adequate counts for imaging. The imaging-effective dosage amounts described herein refer to total amounts administered; that is, if more than one dose of a Radiolabeled Compound is administered, the imaging-effective dosage amounts correspond to the total amount administered.

Kits

The invention encompasses kits that can simplify the administration of a Radiolabeled Compound to a subject.

A typical kit of the invention comprises a unit dosage form of a Radiolabeled Compound.

In one embodiment the unit dosage form is within a container, which can be sterile, containing a therapeutically effective amount of a Radiolabeled Compound and a physiologically acceptable carrier or vehicle. The kit can further comprise a label or printed instructions instructing the use of the Radiolabeled Compound to (i) treat or prevent a disorder in a subject, or (ii) stabilize the mood of a subject having a mood disorder.

In another embodiment the unit dosage form is within a container, which can be sterile, containing an imaging-effective amount of a Radiolabeled Compound and a physiologically acceptable carrier or vehicle. The kit can further comprise a label or printed instructions instructing the use of the Radiolabeled Compound as an imaging agent in order to image or detect one or more 5-HT$_{1A}$ receptors in a subject.

Kits of the invention can further comprise a device that is useful for administering the unit dosage forms. Examples of such a device include, but are not limited to, a syringe, a drip bag, a patch, an inhaler, and an enema bag.

EXAMPLES

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

General Methods

Proton nuclear magnetic resonance (NMR) spectra were obtained from Bruker PPX 300 and 400 MHz spectrophotometer. Spectra are recorded in CDCl$_3$ and the chemical shifts are reported in parts per million relative to TMS for $^1$H NMR as internal standards. The mass spectra were recorded on JKS-HX 11UHF/HX110 HF Tandem Mass Spectrometer in the FAB+ mode. Flash column chromatography was performed on silica gel (Fisher 200-400 mesh) using the solvent system indicated. The radiochemical and chemical purities were analyzed by RP-HPLC with PDA and NaI detectors.

Example 1

Preparation of Compound A

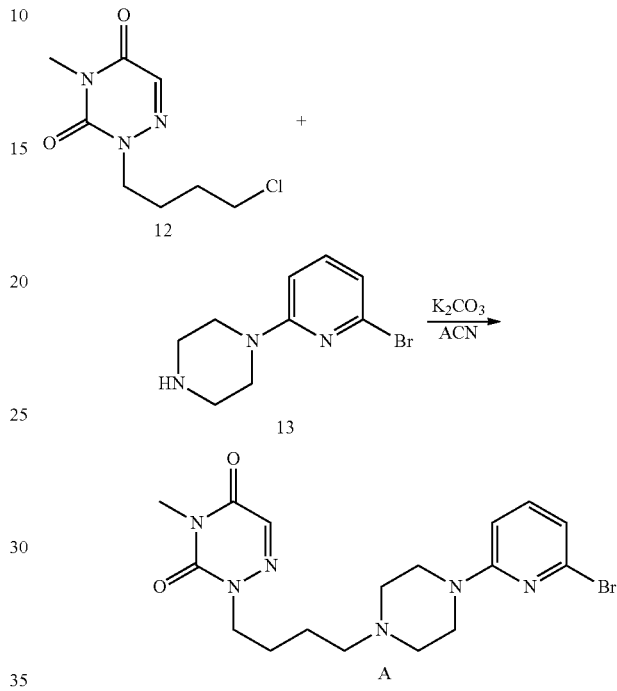

A mixture of 2-(4-chlorobutyl)-4-methyl-1,2,4-triazine-3,5(2H,4H)-dione (12) (217 mg, 1 mmol) and NaI (225 mg, 1.5 mmol) in acetonitrile (3 mL) was stirred under reflux for 30 min. Then, 1-(6-bromopyridin-2-yl)piperazine (360 mg, 1.5 mmol) and anhydrous K$_2$CO$_3$ (420 mg, 3 mmol) were added. The reaction mixture was stirred at 60° C. for 24 h. After cooling, the reaction mixture was diluted with EtOAc, and filtered to remove excess K$_2$CO$_3$. The organic layer was dried over anhydrous MgSO$_4$ and the solvent was removed under vacuum. The crude mixtures were purified by silica gel column chromatography using chloroform/methanol 98:2 (v/v) as the eluent. The combined product fractions were concentrated to yield compound A (340 mg, 80%).

Example 2

Preparation of Compound B

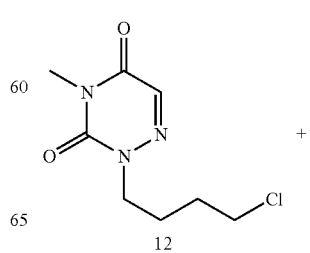

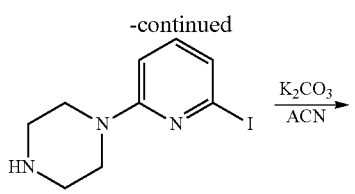

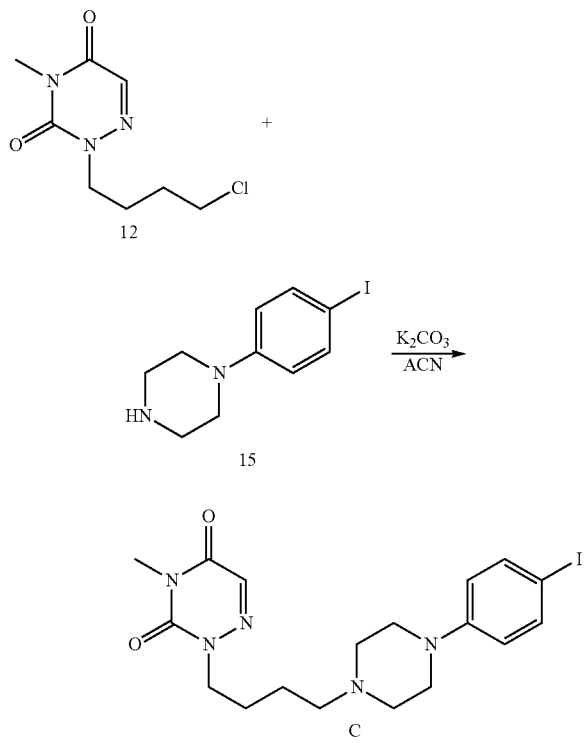

A mixture of 2-(4-chlorobutyl)-4-methyl-1,2,4-triazine-3,5(2H,4H)-dione (12) (217 mg, 1 mmol) and NaI (225 mg, 1.5 mmol) in acetonitrile (3 mL) was stirred under reflux for 30 min. Then, 1-(6-iodopyridin-2-yl)piperazine (440 mg, 1.5 mmol) and anhydrous $K_2CO_3$ (420 mg, 3 mmol) were added. The reaction mixture was stirred at 60° C. for 24 h. After cooling, the reaction mixture was diluted with EtOAc, and filtered to remove excess $K_2CO_3$. The organic layer was dried over anhydrous $MgSO_4$ and the solvent was removed under vacuum. The crude mixtures were purified by silica gel column chromatography using chloroform/methanol 96:4 (v/v) as the eluent. The combined product fractions were concentrated to yield compound B a colorless solid (350 mg, 75%).

Example 3

Preparation of Compound C

A mixture of 2-(4-chlorobutyl)-4-methyl-1,2,4-triazine-3,5(2H,4H)-dione (12) (217 mg, 1 mmol) and NaI (225 mg, 1.5 mmol) in acetonitrile (3 mL) was stirred under reflux for 30 min. Then, 1-(4-iodophenyl)piperazine (435 mg, 1.5 mmol) and anhydrous $K_2CO_3$ (420 mg, 3 mmol) were added. The reaction mixture was stirred at 60° C. for 24 h. After cooling, the reaction mixture was diluted with EtOAc, and filtered to remove excess $K_2CO_3$. The organic layer was dried over anhydrous $MgSO_4$ and the solvent was removed under vacuum. The crude mixtures were purified by silica gel column chromatography using chloroform/methanol 98:2 (v/v) as the eluent. The combined product fractions were concentrated to yield the compound C (380 mg, 80%).

Example 4

Preparation of Compound D

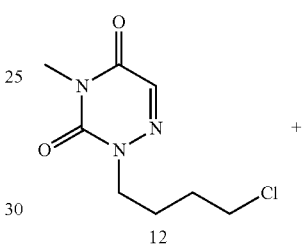

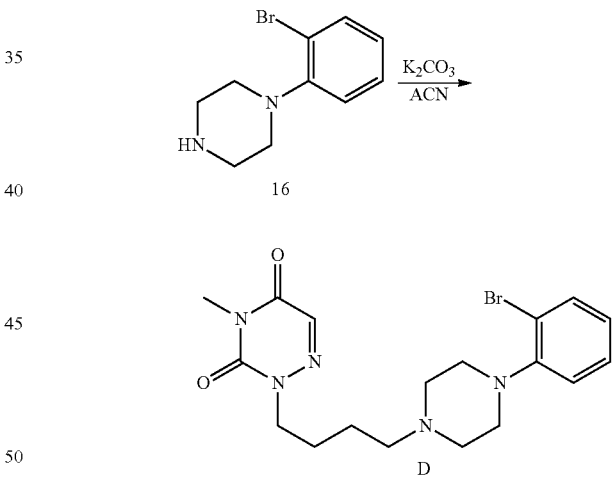

A mixture of 2-(4-chlorobutyl)-4-methyl-1,2,4-triazine-3,5(2H,4H)-dione (12) (217 mg, 1 mmol) and NaI (225 mg, 1.5 mmol) in acetonitrile (3 mL) was stirred under reflux for 30 min. Then, 1-(2-bromophenyl)piperazine (360 mg, 1.5 mmol) and anhydrous $K_2CO_3$ (420 mg, 3 mmol) were added. The reaction mixture was stirred at 60° C. for 24 h. After cooling, the reaction mixture was diluted with EtOAc, and filtered to remove excess $K_2CO_3$. The organic layer was dried over anhydrous $MgSO_4$ and the solvent was removed under vacuum. The crude mixtures were purified by silica gel column chromatography using chloroform/methanol 98:2 (v/v) as the eluent. The combined product fractions were concentrated to yield the compound C (290 mg, 70%).

Example 5

Preparation of Compound E

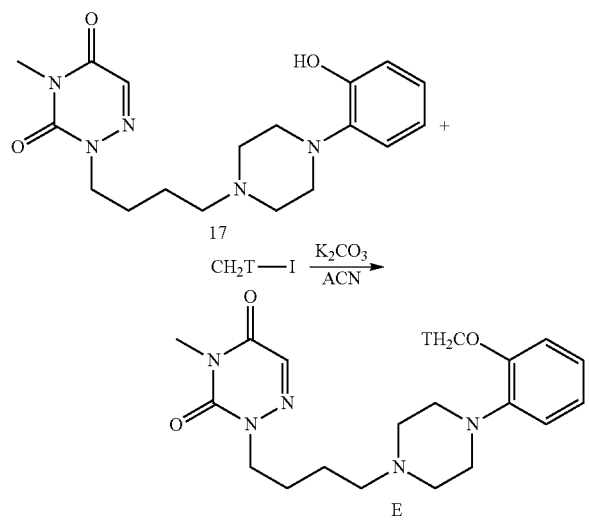

The compound E was synthesized as follows. Precursor compound 17 (1.0 mg) was placed in a vial. To the vial was added acetonitrile (500 μL), followed by 40 mg $K_2CO_3$ (0.3 mmol). The resulting solution was allowed to stand for 5 minutes, then $CH_2{}^3H$—I was added and the reaction mixture was heated at 60° C. for 5 minutes. The crude product was directly injected onto a semi preparative RP-HPLC column (Phenomenex C18, 10 mm×250 mm) and was eluted at a flow rate of 10 mL/min using a mobile phase of acetonitrile:0.1 M aqueous ammonium formate (40:60). Compound E was eluted at 8-9 minutes and the fractions containing Compound E were collected, diluted with deionized water (100 μL added to each fraction), and combined. The combined diluted fractions were filtered through a C-18 Sep-Pak cartridge and concentrated in vacuo to provide Compound E.

Example 6

Ex-Vivo and In Vitro Binding Studies of Compounds A, B, C, D, and E

Binding studies of Compounds A, B, C, and D were carried out as follows:

In Vitro Agonist Binding Assay.

Preparation of Membrane Fractions from CHO-h5-$HT_{1A}$ Cells. Membranes from CHO cells stably expressing the human 5-$HT_{1A}$ receptor at a density of 8 pmol/mg membrane protein with 5-$HT_{2c}$ receptor background were prepared. Cells were grown in DMEM/F-12 medium supplemented with 5% fatal bovine serum, 50 ig/mL geneticin, and 50 ig/mL hygromycin B in a humidified atmosphere of 5% $CO_2$ until they reached confluence. Cells were harvested by centrifugation (800 g for 5 min) and homogenized using a polytron homogenizer (Polytron, CH-6010 Kreiens-Lu, Brinkman Instrument, Westbury, N.Y.) in buffer containing 20 mM HEPES, pH7.4, 3 mM $MgCl_2$, and a cocktail of protease inhibitors (Sigma-Aldrich, St. Louis, Mo.) at 1:2000 dilution. The homogenate was centrifuged (Beckman Optima LE80K Ultracentrifuge) at 100 000 g for 15 min at 4° C. The pellet was suspended in the same buffer and recentrifuged. The final pellet was suspended in assay buffer containing 20 mM HEPES, pH 7.4, 3 mM $MgCl_2$, 100 mM NaCl, and a mixture of protease inhibitors and stored at −70° C. Protein concentration was determined by detergent compatible colorimetric assay using DC Protein Assay Reagents as recommended by the manufacturer (Bio-Rad, Hercules, Calif.).

Inhibition of [$^3$H]-8-OH-DPAT Binding by A-D or 5-HT in Membranes. For inhibition experiments, the incubation medium consisted of 20 mM HEPES, pH 7.4, 4 mM $CaCl_2$, 5 nM [$^3$H]-8-OH-DPAT, and 30 μg of membrane protein in the presence of different concentrations of 10 or 5-HT. The assay mixture was incubated for 10 min at 30° C. The reaction was terminated by rapid filtration through Whatman GF/B filters followed by three washes with ice cold 20 mM HEPES buffer, pH 7.4, using a cell harvester (Brandel, M-24R Gaitherburg, Md.). Bound radioactivity was determined by liquid scintillation spectrometry (Beckman).

Binding affinity values ($K_i$) were measured and found to be as follows:

| Compound | Binding affinity value ($K_i$) |
|---|---|
| A: | 4 nM |
| B: | 5.5 nM |
| C: | 58.3 nM |

-continued

| Compound | Binding affinity value ($K_i$) |
|---|---|
| D: 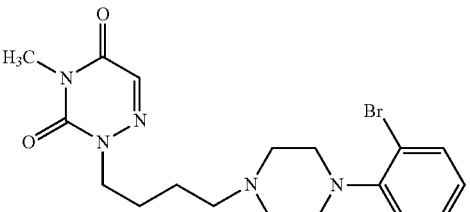 | 6 nM |
| E: 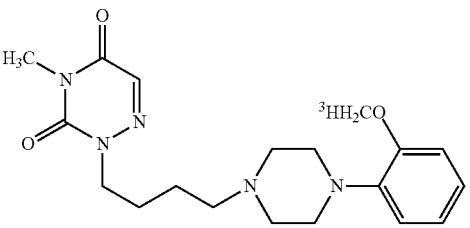 | 0.15 nM |

Example 7

Ex vivo studies of compound E: Awake rats were injected in the tail vein with Compound E shown below:

Compound E

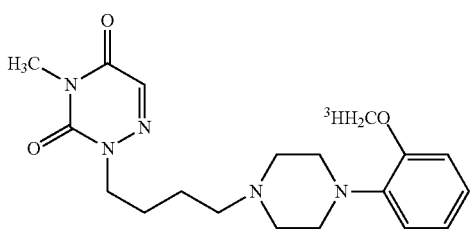

Total mass injected was between 0.02 nmol/kg and 500 nmol/kg. All rats were decapitated after 90 minutes, based on time activity experiments with Compound E. The brains were extracted and brain regions were dissected, and then dissolved in Solvable (Packard). Blood was collected, and the plasma was separated. Radioactivity concentrations were determined by scintillation counting.

It was possible to saturate the 5-HT$_{1A}$ binding of Compound E in the frontal cortex and hippocampus. Data were best fitted with a one binding-site model. The Kd of Compound E was similar for the hippocampus and frontal cortex, with 17-18 nM. The cerebellum and plasma were unsaturable and no binding model could be fitted to the data. Compound E displayed the highest maximal binding in hippocampus with a Bmax of 131 fmol receptors/mg tissue (wet weight) (R2=0.76) and lower maximal binding in the frontal cortex with a Bmax of 98 fmol/mg (R2=0.96).

The results indicate that compound E can be useful for in vitro/ex vivo binding of 5-HT$_{1AR}$.

Example 8

Endogenous changes of 5-HT measurement with Compound E: Rats were pretreated according to the group below, injected with 0.1 MBq (0.18±0.02 nmol/kg, i.v.) of Compound E, then killed by decapitation after 90 minutes. Blood was collected from the trunk, the brain was extracted and the striatum, hippocampus, frontal cortex and cerebellum were dissected. Brain regions were dissolved, plasma was separated from the blood and radioactivity concentrations were determined.

The uptake and binding of Compound E after injection differed by treatment condition. Significant changes in uptake were seen with Fenfluramine 1 and 2, Singly Housed+pCPA, Isoflurane and Isoflurane+Citalopram. Changes in the specific binding ratio (SBR=(activity in ROI−activity in Cerebellum)/activity in Cerebellum) were significant in Fenfluramine 1 and 2.

| | | | Hippocampus Values | |
|---|---|---|---|---|
| Group | Timing | Amount | SUV | SBR |
| Saline | 60 min i.p. | 100 µL/kg | 0% | 0% |
| Citalopram | 60 min i.p. | 4 mg/kg | +4.8% | −12.2% |
| Fenfluramine | 60 min i.p. | 10 mg/kg | −0.1% | +32.8% |
| Single Housed + Saline | 24 h i.p. | 100 µL/kg | −10.0% | −9.2% |
| Single Housed + pCPA | 24 h i.p. | 190 mg/kg | −14.1% | −15.1% |
| Isoflurane, 1-3% (Inhaled) + Saline | 5 min i.p. | 100 µL/kg | +52.1% | −4.6% |
| Isoflurane, 1-3% (Inhaled) + Citalopram | 5 min i.p. | 4 mg/kg | +56.5% | −0.7% |

The results indicate that Compound E is susceptible to pharmacological challenge and may be an indicator of endogenous synaptic transmitter level.

Example 9

Synthesis, pharmacological, radiochemistry and in vivo studies using Compound F:

Several fluoro analogues of various 5-HT$_{1A}$R agonists have been developed as PET ligands [See, e.g., *J. Med. Chem*, 2006, 49, 125-134; *Bioorg. Med. Chem. Lett.* 2006, 16, 2101-2104; *Eur. J. Nuc. Med. Mol. Imaging*, 2007, 34, 1050-1060; *J. Labeled Comp. Radiopham*, 51, 132-136; *J. Nuc. Med.*, 49, 587-596; JCBFM, 2011, 31 (1), 243-249; and JNM 2010, 51 (12), 1892-1900]. Among these, 18 a fluoroethyl analogue of 19 shows 0.1 nM binding affinity ($K_i$) to 5-HT$_{1A}$R. The reference standard 18 was synthesized by reacting bromoethylfluoride with 17 in 65% yield. Synthesis of 17 was achieved by using a procedure developed previously [See, e.g., *J. Med. Chem*, 2006, 49, 125-134; *Bioorg. Med. Chem. Lett.* 2006, 16, 2101-2104; *Eur. J. Nuc. Med. Mol. Imaging*, 2007, 34, 1050-1060; *J. Labeled Comp. Radiopham*, 51, 132-136].

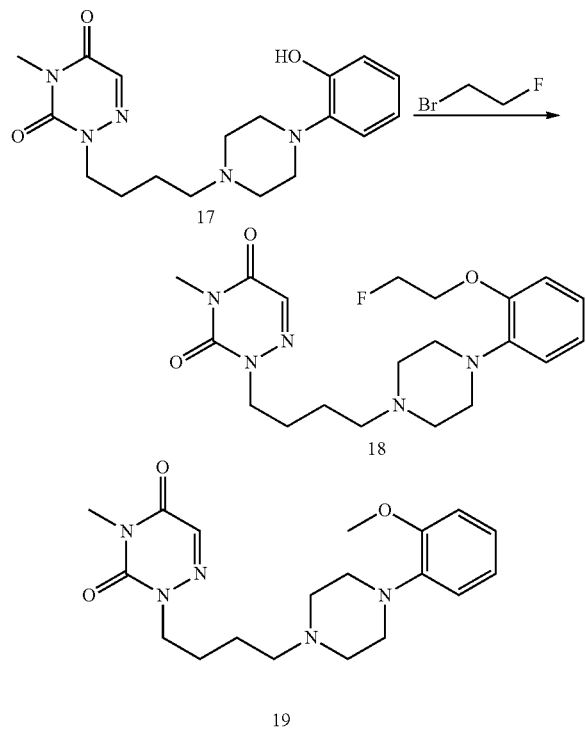

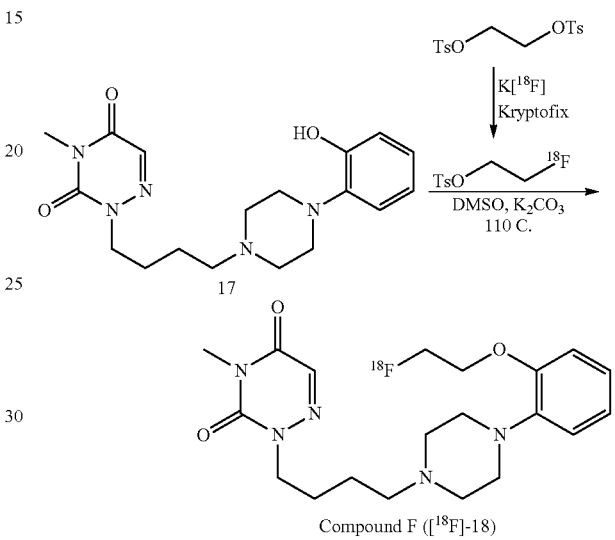

Compound F ([$^{18}$F]-18)

The affinity of 18 for various biogenic amines, brain receptors, and transporters was determined through National Institute of Mental Health Psychoactive Drug Screening Program (NIMH-PDSP). Compound 18 has a $K_i$ of 21.4±0.6 nM for alpha1AR, which is 214 times higher than $K_i$ of 5-HT$_{1A}$R. This is much better than the $K_i$ of compound 19 for alpha$_{1A}$R is 6.75 nM, which is only 45 times higher than $K_i$ of 5-HT$_{1A}$R. Compound 18 also exhibits nanomolar affinity for 5-HT$_7$ (Ki=17.2 nM), D$_2$ (Ki=37.1 nM), D$_3$ (Ki=22 nM) and D$_4$ (Ki=71 nM) receptors. Whereas, $K_i$ values for these receptors for compound 19 were 12.9 nM, >10,000 nM, >10,000 nM, 21.8 nM respectively. The numbers of 5-HT$_7$ and D$_4$ receptors are too low in brain to be detected using PET. Another noticeable advantage of compound 18 vs compound 19 is its >10,000 nM $K_i$ to sigma 1R in comparison to a $K_i$ of 59 nM for compound 19. The $K_i$ values for various other brain receptors and transporters were low (0.1 to 10 µM). Agonist properties of compound 18 on 5-HT$_{1A}$R were evaluated using [$^{35}$S] GTPγS binding in membranes of CHO cells stably expressing the human 5-HT$_{1A}$R. Compound 18 produced a dose-dependent increase in [$^{35}$S]GTPγS binding. Maximal compound 18 stimulated [$^{35}$S]GTPγS binding E$_{max}$ was 80% of that seen with 5-HT, which is comparable to the E$_{max}$ of compound 19.

Radiosynthesis of Compound F ([$^{18}$F]-18) was performed by a two step fluoroalkylation of the phenolate of 17. For this purpose, [$^{18}$F]fluoroethyltosylate was initially synthesized by radioflurination of ethyleneglycol ditosylate with K[$^{18}$F], kryptofix and K$_2$CO$_3$ in 90% yield. [$^{18}$F]fluoroethyltosylate ([$^{18}$F]FCH$_2$—CH$_2$OTs) was purified via semiprep-HPLC and reacted with 17 in presence of base afford Compound F ([$^{18}$F]-18). Improvements in the yield of compound F from 5% to 50% have been observed by modifying the reaction conditions such as using LiChrolut EN column instead of C-18 Seppak to trap [$^{18}$F]Fluoroethyltosylate and changing the base from 5M NaOH to 5% K$_2$CO$_3$. The crude product was purified by RP-HPLC followed by C-18 Sep-Pak® purification to obtain Compound F in 45+5% yield at EOS (n=10). Specific activity obtained for Compound F was 2,500±500 Ci/mmol (n=8) based on a standard mass curve with >95% chemical and radiochemical purities. The total time required for the radiolabeling process was 60 min at EOS. Compound F may alternatively be synthesized in one step from the corresponding tosylate. The lopP$_{o/w}$, of Compound F from shake flask method was found to be 1.2. The stability of Compound F formulation (10% ethanol-90% saline) used for in vivo studies was analyzed up to 4 hours using analytical HPLC and radio-TLC and found the radioproduct was stable up to 4 h with no significant de[$^{18}$F] fluorination in the formulation.

Figure 2:
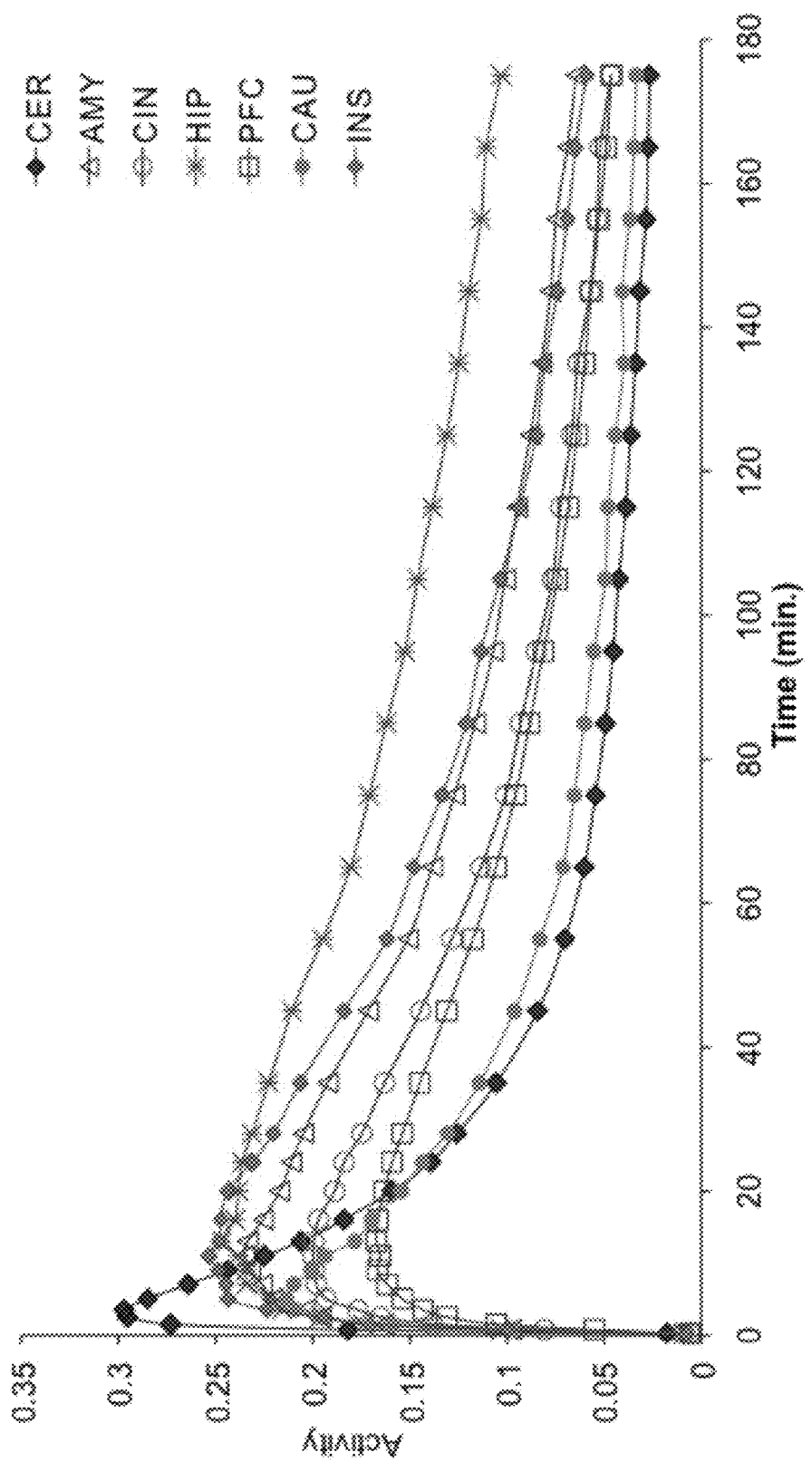
FIG. 2: Time activity curves of the radioactivity in baboon after the injection of Compound F. AMY=Amygdala, CAU=Caudate, CER=cerebellum, CIN=cingulate, HIP=hippocampus, PFC=prefrontal cortex.
Figure 3:
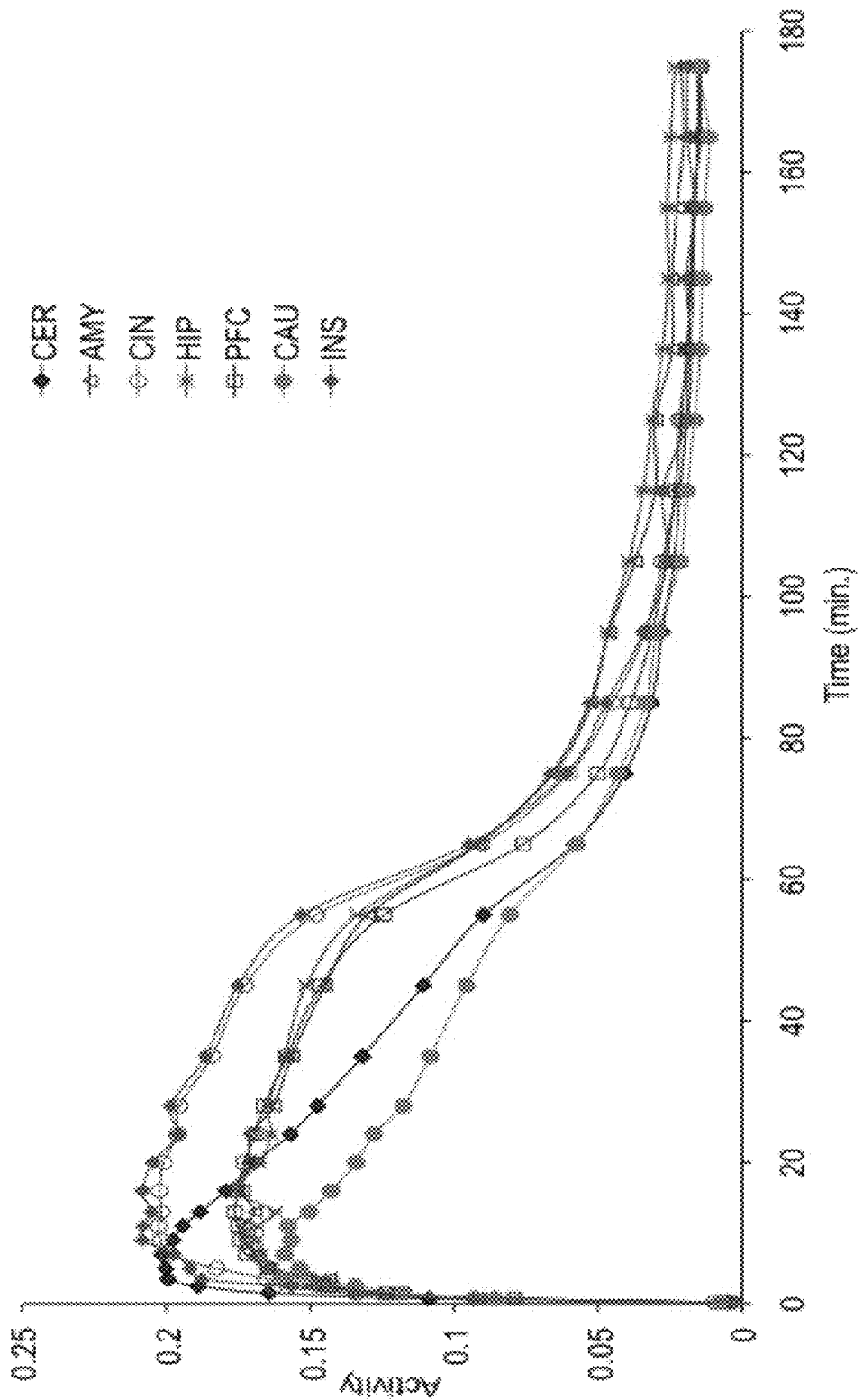
FIG. 3: Time activity curves of the radioactivity of Compound F in baboon followed by 30 minute post injection of WAY-100635 (0.5 mg/kg, i.v).

In Vivo Studies:

PET studies in anesthetized baboon (*Papio anubis*) showed that Compound F (3.5+1 mCi) penetrated the blood-brain-barrier (BBB) and was retained in 5-HT$_{1A}$R rich areas such as hippocampus, insula, cingulate, prefrontal cortex, and amygdala, whereas the striatum exhibited lower binding and cerebellum had the least amount of binding (FIG. 1). No skull image due to radio[$^{18}$F]defluorination was observed. Radioactivity in all regions reached a peak by 3 to 13 min post injection and a rapid clearance was observed for cerebellum. The respective binding ratios of hippocampus, insula, cingulate, prefrontal cortex, and amygdala, to cerebellum were 4.0, 2.3, 1.8, 1.8, and 2.4 at 175 min. The specificity of the ligand uptake was determined by chase studies with the WAY-100635 (0.5 mg/kg/i.v) between 50-60 minutes after the administration of Compound F (FIGS. 2 and 3). Protein binding of Compound F was 35±1.5% (n=12) and 11.5±2.5% (n=12) in baboon and human plasma samples respectively. HPLC analyses of the plasma samples indicated only polar metabolites and the percentage of unmetabolized Compound F was 98±1.0% at 2 min, 74±2.5% at 12 min, 51% at 30 min 37±4.0% at 60 min, 32.5±0.5% at 90 min, 23.5±2% at 120 min, 21.5±2% at 150 min and 18±2% at 190 minutes respectively. No significant changes in metabolism were observed in the chase challenge administration (50-60 min). The TACs shows that radioligand reached equilibrium in 40 min, and a 120 minute scan may be suitable for baboon PET studies with Compound F.

Upon review of the description and embodiments of the present invention, those skilled in the art will understand that modifications and equivalent substitutions may be performed

The invention claimed is:

1. A compound having the formula:

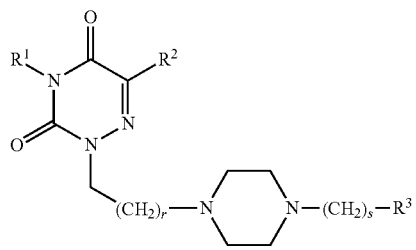
(Ia)

or a pharmaceutically acceptable salt thereof,
wherein:
  r and s are each independently an integer ranging from 0 to 3;
  $R^1$ is —$C_1$-$C_6$ alkyl,
  $R^2$ is —H, and
  $R^3$ is -aryl, -heteroaryl or -napththyl, each of which is substituted with $^{75}$Br, $^{76}$Br, $^{120}$I, $^{123}$I, $^{124}$I, $^{125}$I, $^{131}$I, or —O$C^3$H$H_2$.

2. The compound of claim 1, the compound having the formula

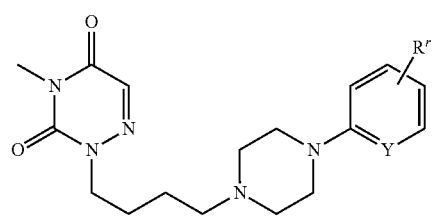
(Ib)

or pharmaceutically acceptable salts thereof, wherein Y is —CH— or —N— and $R^r$ is —O$C^3$H$H_2$, $^{75}$Br, $^{76}$Br, $^{120}$I, $^{123}$I, $^{124}$I, $^{125}$I or $^{131}$I.

3. The compound of claim 1, wherein $R^1$ is methyl.

4. The compound of claim 1, having the formula:

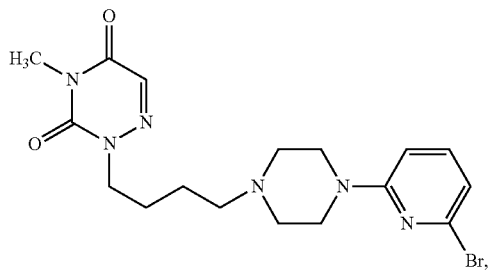

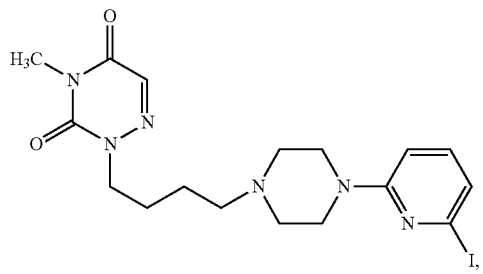

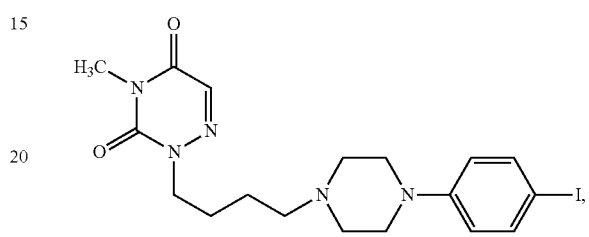

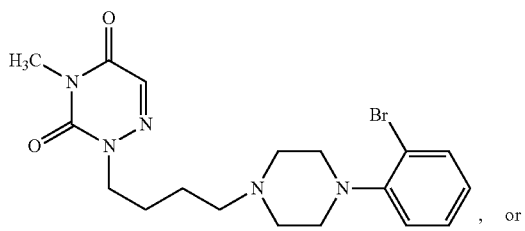

or a pharmaceutically acceptable salt thereof, wherein Br is $^{75}$Br or $^{76}$Br and I is $^{120}$I, $^{123}$I, $^{124}$I, $^{125}$I or $^{131}$I.

5. The compound of claim 4, wherein the compound is

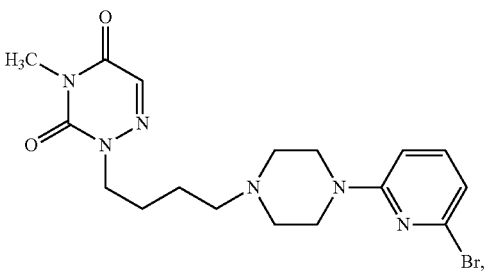

or a pharmaceutically acceptable salt thereof, wherein Br is $^{75}$Br or $^{76}$Br.

6. The compound of claim 4, wherein the compound is

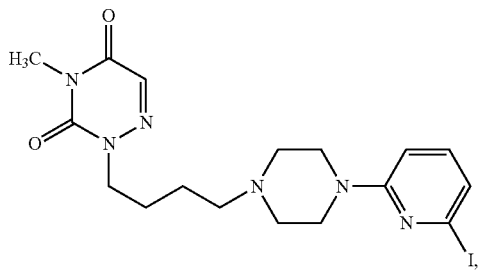

or a pharmaceutically acceptable salt thereof, wherein I is $^{120}$I, $^{123}$I, $^{124}$I, $^{125}$I or $^{131}$I.

7. The compound of claim 4, wherein the compound is

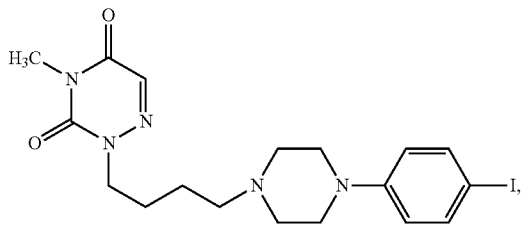

or a pharmaceutically acceptable salt thereof, wherein I is $^{120}$I, $^{123}$I, $^{124}$I, $^{125}$I or $^{131}$I.

8. The compound of claim 4, wherein the compound is

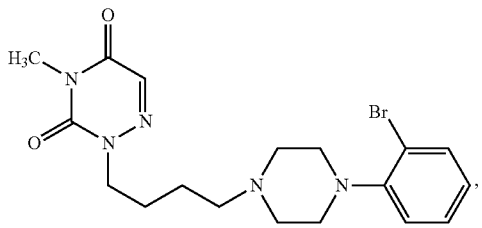

or a pharmaceutically acceptable salt thereof, wherein Br is $^{75}$Br or $^{76}$Br.

9. The compound of claim 4, wherein the compound is

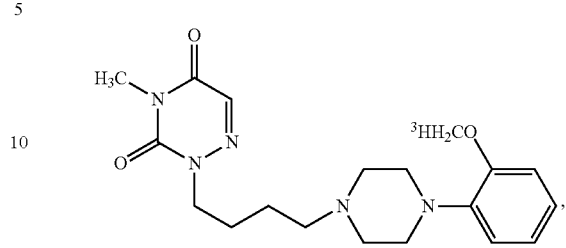

or a pharmaceutically acceptable salt thereof.

10. A compound having the formula:

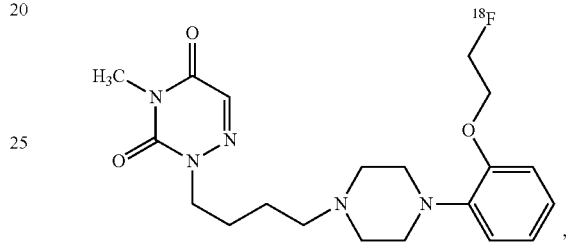

or a pharmaceutically acceptable salt thereof.

11. A composition comprising a therapeutically effective amount of a compound of claim 1 or 10, or a pharmaceutically acceptable salt thereof, and a physiologically acceptable carrier or vehicle.

12. A composition comprising an imaging-effective amount of a compound of claim 1 or 10, or a pharmaceutically acceptable salt thereof, and a physiologically acceptable carrier or vehicle.

13. A composition comprising a physiologically acceptable salt and the compound of claim 1 or 10, or a pharmaceutically acceptable salt thereof.

* * * * *